(12) United States Patent
Wong et al.

(10) Patent No.: US 6,921,810 B2
(45) Date of Patent: Jul. 26, 2005

(54) BIFUNCTIONAL ANTIBIOTICS

(75) Inventors: Chi-Huey Wong, Rancho Santa Fe, CA (US); Steven Sucheck, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 10/258,504

(22) PCT Filed: Apr. 27, 2001

(86) PCT No.: PCT/US01/40611

§ 371 (c)(1),
(2), (4) Date: Mar. 28, 2003

(87) PCT Pub. No.: WO01/80863

PCT Pub. Date: Nov. 1, 2001

(65) Prior Publication Data

US 2003/0181399 A1 Sep. 25, 2003

Related U.S. Application Data

(60) Provisional application No. 60/200,084, filed on Apr. 27, 2000.

(51) Int. Cl.[7] ..................... C07H 15/02; A61K 31/7016
(52) U.S. Cl. ......................... 536/17.9; 536/17.2; 514/25
(58) Field of Search .......................... 514/25; 536/17.2, 536/17.9

(56) References Cited

PUBLICATIONS

Wang, H. et al. Bioorganic & Medicinal Chemistry Letters 1997, 7(14), 1951–1956.*
Tok, J.B–H. et al. Bioorganic & Medicinal Chemistry Letters Jul. 17, 2000, 10, 1593–1595.*
Sucheck, S.J. et al. J. Am. Chem. Soc. published on the Web May 16, 2000, 122, 5230–5231.*
Patterson, et al., "High–Level Gentamicin Resistance in *Enterococcus*: Microbiology, Genetic Basis, and Epidemiology", *Rev. Infect. Diseases* 12: 644–652 (1990).
Edson, et al., "The Aminoglycosides", *Mayo Clin. Proc.* 66: 1158–1164 (1991).
Kondo, et al., "Semisynthetic aminoglycoside antibiotics: Development and enzymatic modifications", *J. Infect. Chemother.* 5: 1–9 (1999).
Moazed, et al., "Interaction of antibiotics with functional sites in 16S ribosomal RNA", *Nature* 327: 389–394 (1987).
Purohit, et al., "Interactions of a small RNA with antibiotic and RNA ligands of the 30S subunit", *Nature* 370: 659–662 (1994).
Sundram, et al., "Novel Vancomycin Dimers with Activity against Vancomycin–Resistant Enterococci", *J. Am. Chem. Soc.* 1996: 13107–13108 (1996).
Fourmy, et al., "Structure of the A Site of *Escherichia coli* 16S Ribosomal RNA Complexed with an Aminoglycoside Antibiotic", *Science* 274: 1367–1371 (1996).

Azucena, et al., "Properties of a Bifunctional Bacterial Antibiotic Resistance Enzyme That Catalyzes ATP–Dependent 2"–Phosphorylation and Acetyl–CoA–Dependent 6'–Acetylation of Aminoglycosides", *J. Am. Chem. Soc.* 119: 2317–2318 (1997).
Hendrix, et al., "Direct Observation of Aminoglycoside–RNA Interactions by Surface Plasmon Resonance", *J. Am. Chem. Soc.* 119: 3641–3648 (1997).
Rao, et al., "Tight Binding of a Dimeric Derivative of Vancomycin with Dimeric L–Lys–D–Ala–D–Ala", *J. Am. Chem. Soc.* 119: 10286–10290 (1997).
Wong, et al., "Specificity of aminoglycoside antibiotics for the A–site of the decoding region of ribosomal RNA", *Chem. Biol.* 5: 397–406 (1998).
Wright, et al., "Aminoglycoside Antibiotics: Structures, Functions, and Resistance", *Adv. Exp. Med. Biol.* 456: 27–69 (1998).
Mingeot–Leclerco, et al., "Aminoglycosides: Activity and Resistance", *Antimicrobial Agents and Chemotherapy* 43: 727–737 (1999).

(Continued)

*Primary Examiner*—Leigh C. Maier
(74) *Attorney, Agent, or Firm*—Donald G. Lewis

(57) ABSTRACT

Bifunctional antibiotics that target both bacterial RNA and resistance-causing enzymes are disclosed. The A-site of bacterial 16S rRNA serves as the target site for most aminoglycoside antibiotics. Resistance to this class of antibiotics is frequently developed by microbial enzymatic acetylation, phosphorylation or ribosylation of aminoglycosides, modifications that weaken their interactions with the target RNA. Using surface plasmon resonance (SPR), the binding affinity and stoichiometry of various amino-glycosides have been investigated and it was found that neamine, the key pharmacophore of the deoxystreptamine class of amino-glycosides, binds to the A-site in a two to one stoichiometry with a $K_d$ of 10 $\mu$M for each binding site. A library of neamine dimers was prepared and their affinities to 16S rRNA A-site were determined by SPR, with $K_d$=40 nM for the best dimer (an ~$10^3$-fold increase in affinity). Antibiotic activities of the dimers were determined for several bacterial strains by the Kirby-Bauer method. The most active dimer, based on antibiotic activity, also showed the highest inhibition of in vitro translation ($IC_{50}$=0.055 $\mu$M). The latter assay was developed in order to correlate the relationship between SPR-based affinity and translation inhibition. By these combined methods, transport limitations for the semisynthetic aminoglycosides as well as non-ribosomally based antibiotic activity could be determined. Further analysis of these dimers as substrates for aminoglycoside modifying-enzymes identified a neamine dimer that was a potent inhibitor ($K_{is}$=0.1 $\mu$M) of the APH(2") activity of the bifunctional enzyme AAC(6")-APH(2"), the primary enzyme responsible for high level gentamicin C resistance in several bacterial strains.

13 Claims, 13 Drawing Sheets

OTHER PUBLICATIONS

Daigle, et al., "Prodigious substrate specificity of AAC(6')–APH(2"), an aminoglycoside antibiotic resistance determinant in enterococci and staphylococci", *Chem. Biol.* 6: 99–110 (1999).

Greenburg, et al., "Design and Synthesis of New Aminoglycoside Antibiotics Containing Neamine as an Optimal Core Structure: Correlation of Antibiotic Activity with in Vitro Inhibition of Translation", *J. Am. Chem. Soc.* 121: 6527–6541 (1999).

Michael, et al., "Enhanced RNA Binding of Dimerized Aminoglycosides", *Bioorg. Med. Chem.* 7: 1361–1371 (1999).

* cited by examiner

GC base Pair    phosphodiester

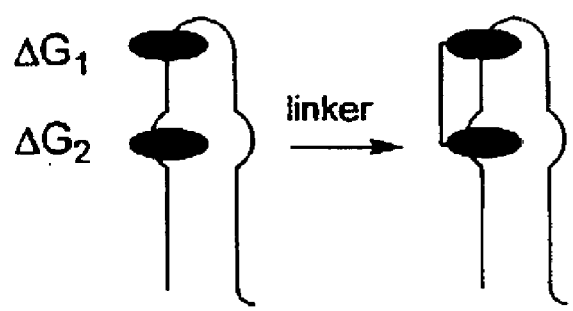
$$\Delta G_T = \Delta G_1 + \Delta G_2 + \Delta G_{Linker}$$
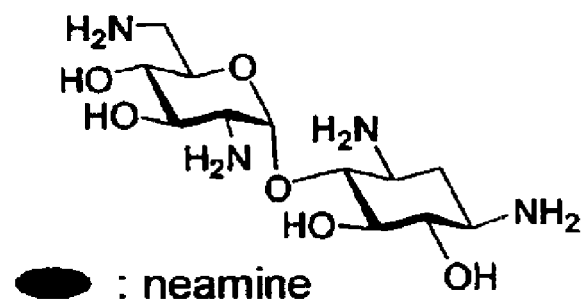
● : neamine
Figure 4

Kirby Bauer Tests: diameters (in mm) of zones of inhibition for test strains. All compounds except neomycin and gentamicin were spotted at 200nmoles/disk; neomycin was spotted at 33nmoles/disk (30μg) while gentamicin was spotted at 10nmol/disk (10μg). SPR $K_d$ values for dimers 4-13 is also provided.

| compound | E. coli ATCC 25922 | S. aureus ATCC 25923 | $K_d$ (μM) |
| --- | --- | --- | --- |
| neamine (1) | 17 | 17 | 10 |
| neomycin (2) | 18.5 | 21 | 0.2 |
| gentamicin (3) | 19.5 | 20 | 1.7 |
| ribostamycin | 16.5 | 14.5 | 25 |
| paromomycin | 18 | 19.5 | 0.2 |
| 4 | 14.5 | 20 | 1.1 |
| 5 | 14 | 17.5 | 4.6 |
| 6 | 12.5 | 17.5 | 0.8 |
| 7 | 10.5 | 14 | 4.4 |
| 8 | 11 | 14.5 | 4.1 |
| 9 | 10.5 | 14.5 | 2.3 |
| 10 | 10.5 | 14.5 | 2.4 |
| 11 | 13 | 13.5 | 2.8 |
| 12 | 10 | 12.5 | 1.9 |
| 13 | 11 | 8.5 | 21 |
| 14 | 14 | 14 | 5.4 |
| 17 | 16 | 21 | 12 |
| 18 | 15 | 20 | 2.6 |
| 19 | 15 | 19.5 | 17 |
| 20 | 18 | 22.5 | 1.2 |
| 21 | 15 | 20.5 | 0.5 |
| 22 | 16.5 | 21.5 | 0.2 |
| 23 | 13 | 18 | 5.0 |
| 24 | 18 | 21.5 | 1.0 |
| 25 | 11 | 17.5 | 0.6 |
| 26 | 17 | 23 | 0.8 |
| 27 | 18.5 | 21.5 | 0.04 |
| 28 | 16 | 22 | 0.8 |

Figure 11

Minimum Inhibitory Concentration (μM) in *E. Coli* ATCC 25922
and *In Vitro* Translation $IC_{50}$.

| Compound | antibiotic activity (MIC, μM) | translation inhibition ($IC_{50}$, nM) |
|---|---|---|
| neamine (1) | 50-100 | 410 |
| neomycin (2) | 3.1 | 28 |
| gentamicin (3) | 1.6 | 20 |
| ribostamycin | 12.5 | 100 |
| kanamycin | 12.5 | 150 |
| paromomycin | 6.25 | 40 |
| tobramycin | 3.1 | 50 |
| streptomycin | 10 | 150 |
| spectinomycin | 50 | 500 |
| 4 | 31 | 300 |
| 6 | 125 | 1000 |
| 14 | 50 | 860 |
| 17 | 25-50 | 280 |
| 18 | 50 | 550 |
| 19 | 25 | 270 |
| 20 | 12.5 | 200 |
| 21 | 25-50 | 310 |
| 22 | 12.5-25 | 160 |
| 23 | 100 | >500 |
| 24 | 12.5 | 70 |
| 25 | 100 | >500 |
| 26 | 12.5 | 130 |
| 27 | 6.25 | 55 |
| 28 | 25 | 280 |

Figure 12

Kinetic Parameters of Neamine Dimers 6 and Neamine for Various Aminoglycoside Modifying-Enzymes. BF refers to the bifunctional enzyme AAC(6')-APH(2"), where the particular activity tested is indicated.

neamine (1) (Daigle, D. M.; et al. *Chem. Biol.* 1999, *6*, 99)

| Enzyme | $K_M$ | $k_{cat}$ (s$^{-1}$) | $K_{is}$ (µM) | $k_{cat}/K_M$ (M$^{-1}$s$^{-1}$) |
|---|---|---|---|---|
| BF AAC-(6') | 8.40 | 3.00 | 15.0 | 3.6 x 10$^5$ |
| BF APH-(2") | 9.6 | 0.17 | | 1.8 x 10$^4$ | neamine dimer 4

| Enzyme | $K_M$ (µM) | $k_{cat}$ (s$^{-1}$) | $K_{is}$ (µM) | $k_{cat}/K_M$ (M$^{-1}$s$^{-1}$) |
|---|---|---|---|---|
| BF AAC-(6') | 0.84 | | | |
| BF APH-(2") | | | 0.78 | |
| AAC-Ii-(6') | 53.4 | 0.86 | | 1.6 x 10$^4$ |
| APH-(3') | 0.82 | 0.75 | | 9.14 x 10$^5$ | neamine dimer 6

| Enzyme | $K_M$ (µM) | $k_{cat}$ (s$^{-1}$) | $K_{is}$ (µM) | $k_{cat}/K_M$ (M$^{-1}$s$^{-1}$) |
|---|---|---|---|---|
| BF AAC-(6') | 4.22 | 0.967 | | 2.29 x 10$^5$ |
| BF APH-(2") | | | 0.149 | |
| AAC-Ii-(6') | 83.6 | 1.89 | | 2.26 x 10$^4$ |
| APH-(3') | 2.66 | 0.639 | | 2.49 x 10$^5$ | neamine dimer 27

| Enzyme | $K_M$ (µM) | $k_{cat}$ (s$^{-1}$) | $K_{is}$ (µM) | $k_{cat}/K_M$ (M$^{-1}$s$^{-1}$) |
|---|---|---|---|---|
| BF AAC-(6') | 0.53 | | | |
| BF APH-(2") | | | 0.94 | |
| AAC-Ii-(6') | 28.7 | 0.26 | | 9.26 x 10$^3$ |
| APH-(3') | 1.1 | 0.42 | | 3.8 x 10$^5$ |

Figure 13

BIFUNCTIONAL ANTIBIOTICS

CROSS-REFERENCE TO RELATED APPLICATIONS

This is a U.S. national phase application of international application Serial No. PCT/US01/40611, filed Apr. 27, 2001 and published in English, which claims priority from and is a continuation-in-part application of U.S. provisional patent application Ser. No. 60/200,084, filed Apr. 27, 2000.

TECHNICAL FIELD

The invention relates to bifunctional antibiotics. More particularly, the invention related to bifunctional antibiotics that target bacterial rRNA and inhibit resistance-causing enzymes.

BACKGROUND

Deoxystreptamine-based aminoglycosides are a clinically important class of antibiotics that are effective against a broad range of microorganisms (Edson, R. S.; Terrel, C. L. *Mayo Clin. Proc.* 1991, 66, 1158). It is believed that aminoglycosides exert their therapeutic effect by interfering with translational fidelity during protein synthesis via interaction with the A-site rRNA on the 16S domain of the ribosome (Moazed, D.; Noller, H. F. *Nature* 1987, 327, 389; Purohit, P.; Stern, S. *Nature* 1994, 370, 659; Formy, D.; et al. *Science* 1996, 274, 1367). Unfortunately, the high toxicity and rapid emergence of high level aminoglycoside resistance have severely limited the usefulness of this class of antibiotics. Numerous aminoglycoside resistance mechanisms have been identified, and enzymatic acetylation, phosphorylation and ribosylation are the primary causes of high level resistance in most clinical isolates (Wright, G. D.; et al. *Adv. Exp. Med. Biol.* 1998, 456, 27; Kondo, S.; Hotta, K. *J. Infect. Chemother.* 1999, 5, 1; Mingeot-Leclerco, M.-P.; et al. *Antimicrob. Agents Chemother.* 1999, 43, 727). Of the modifying enzymes, the acetyl- and phosphotransferases (AAC and APH) have been extensively studied with respect to their specificity (Wright, G. D.; et al. *Adv. Exp. Med. Biol.* 1998, 456, 27; Kondo, S.; Hotta, K. *J. Infect. Chemother.* 1999, 5, 1; Mingeot-Leclerco, M.-P.; et al. *Antimicrob. Agents Chemother.* 1999, 43, 727; Daigle, D. M.; et al. *Chem. Biol.* 1999, 6, 99; Azucena, E.; et al. *J. Am. Chem. Soc.* 1997, 119, 2317; Patterson, J.-E.; Zervos, M. *J. Rev. Infect. Dis.* 1990, 12, 644).

What was needed was a method to tackle the problem of antibiotic resistance. What was needed was bifunctional aminoglycosides that can resist or inhibit aminoglycoside-modifying enzymes while simultaneously targeting ribosomal RNA.

SUMMARY

Bifunctional antibiotics are disclosed herein that target both bacterial RNA and resistance causing enzymes. Preferred bifunctional antibiotics are disclosed to be neamine dimers. These neamine dimers represent a new class of aminoglycoside antibiotics that are functionally simpler than previously known aminoglycosides. In addition targeting bacterial RNA, they are also potent inhibitors of the APH (2") activity of the bifunctional AAC(6')-APH(2") enzyme, one of the most clinically significant of the aminoglycoside-modifying enzymes.

Bifunctional antibiotics that target both bacterial RNA and resistance-causing enzymes are disclosed and are demonstrated to provide a method for tackling the problem of antibiotic resistance. The A-site of bacterial 16S rRNA serves as the target site for most aminoglycoside antibiotics. Resistance to this class of antibiotics is frequently developed by microbial enzymatic acetylation, phosphorylation or ribosylation of aminoglycosides, modifications that weaken their interactions with the target RNA. Using surface plasmon resonance (SPR), the binding affinity and stoichiometry of various aminoglycosides have been investigated and it was found that neamine, the key pharmacophore of the deoxystreptamine class of aminoglycosides, binds to the A-site in a two to one stoichiometry with a $K_d$ of 10 $\mu$M for each binding site. A library of neamine dimers was prepared and their affinities to 16S rRNA A-site were determined by SPR, with $K_d$=40 nM for the best dimer (an ~$10^3$-fold increase in affinity). Antibiotic activities of the dimers were determined for several bacterial strains by the Kirby-Bauer method. The most active dimer, based on antibiotic activity, also showed the highest inhibition of in vitro translation ($IC_{50}$=0.055 $\mu$M). The latter assay was developed in order to correlate the relationship between SPR-based affinity and translation inhibition. By these combined methods, transport limitations for the semisynthetic aminoglycosides as well as non-ribosomally based antibiotic activity could be determined. Further analysis of these dimers as substrates for aminoglycoside modifying-enzymes identified a neamine dimer that was a potent inhibitor ($K_{is}$=0.1 $\mu$M) of the APH(2") activity of the bifunctional enzyme AAC(6")-APH (2"), the primary enzyme responsible for high level gentamicin C resistance in several bacterial strains.

One aspect of the invention is directed to a bifunctional antibiotic. The bifunctional antibiotic includes a first and a second pharmacophore and a linkage for linking the first and second pharmacophore. The first and second pharmacophore each has a binding affininty for the A-site of bacterial 16S rRNA sufficient to inhibit translation at clinically effective concentrations. The first and second pharmacophores may be either identical to one another or different from one another. The linkage has a length and structure for enabling the first and second pharmacophore to bind simultaneously to a single A-site of bacterial 16S rRNA. In an improved embodiment of the invention, at least one of the first and second pharmacophores is inhibitory of APH(2") activity with respect to bifunctional enzyme AAC(6')-APH(2"). The inhibitory activity is sufficient, at clinically effective concentrations, to diminish deactivation of the bifunctional antibiotic by the bifunctional enzyme AAC(6')-APH(2").

In one embodiment of this aspect of the invention, the bifunctional antibiotic is represented by the following structure:

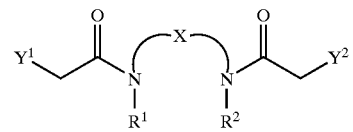

In the above structure, $Y^1$ and $Y^2$ are the first and second pharmacophore respectively and are both represented by:

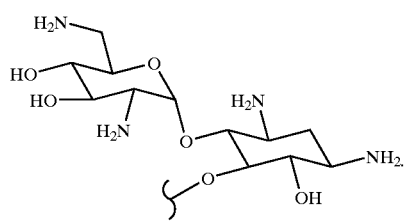

$R^1$ and $R^2$ are each independently selected from the group of radicals consisting of —H and —CH(Ph)CONHCH$_2$CO$_2$H.

X is the linkage and is selected from the group of diradicals consisting of —(CH$_2$)$_n$— and —[(CH$_2$)$_2$O(CH$_2$)$_3$]$_2$O, where $3 \leq n \leq 12$.

In a second embodiment of this aspect of the invention, the bifunctional antibiotic is represented by the following structure:

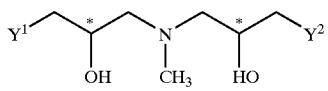

In the above structure, Y$^1$ and Y$^2$ are the first and second pharmacophore respectively and are both represented by:

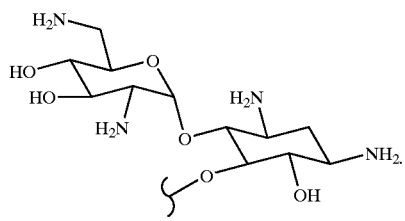

The stereochemistry is either (S,S) or (R,R). Preferred species of this embodiment include compounds represented by the following structures:

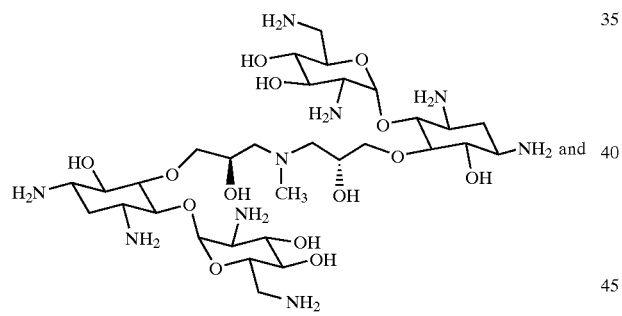

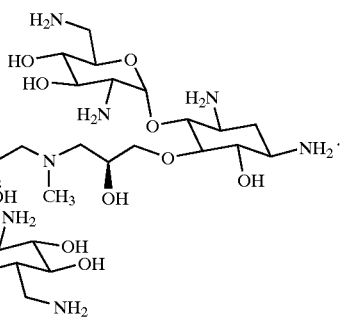

In a third embodiment of this aspect of the invention, the bifunctional antibiotic is represented by the following structure:

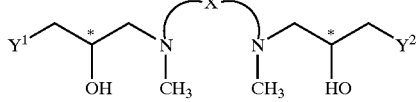

In the above structure, Y$^1$ and Y$^2$ are the first and second pharmacophore respectively and are both represented by:

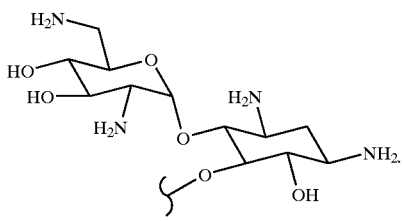

X is the linkage and is selected from the group of diradicals consisting of —(CH$_2$)$_n$— and —[(CH$_2$)$_2$]$_2$O, where $2 \leq n \leq 4$. The stereochemistry is either (S,S) or (R,R). Preferred species of this embodiment include compound represented by the following structures:

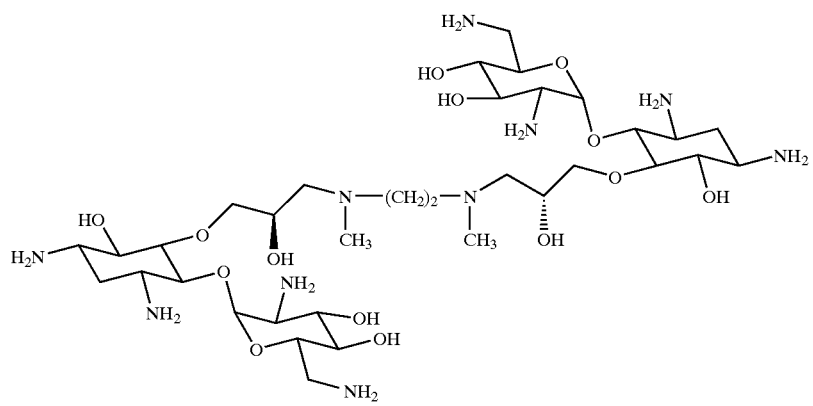

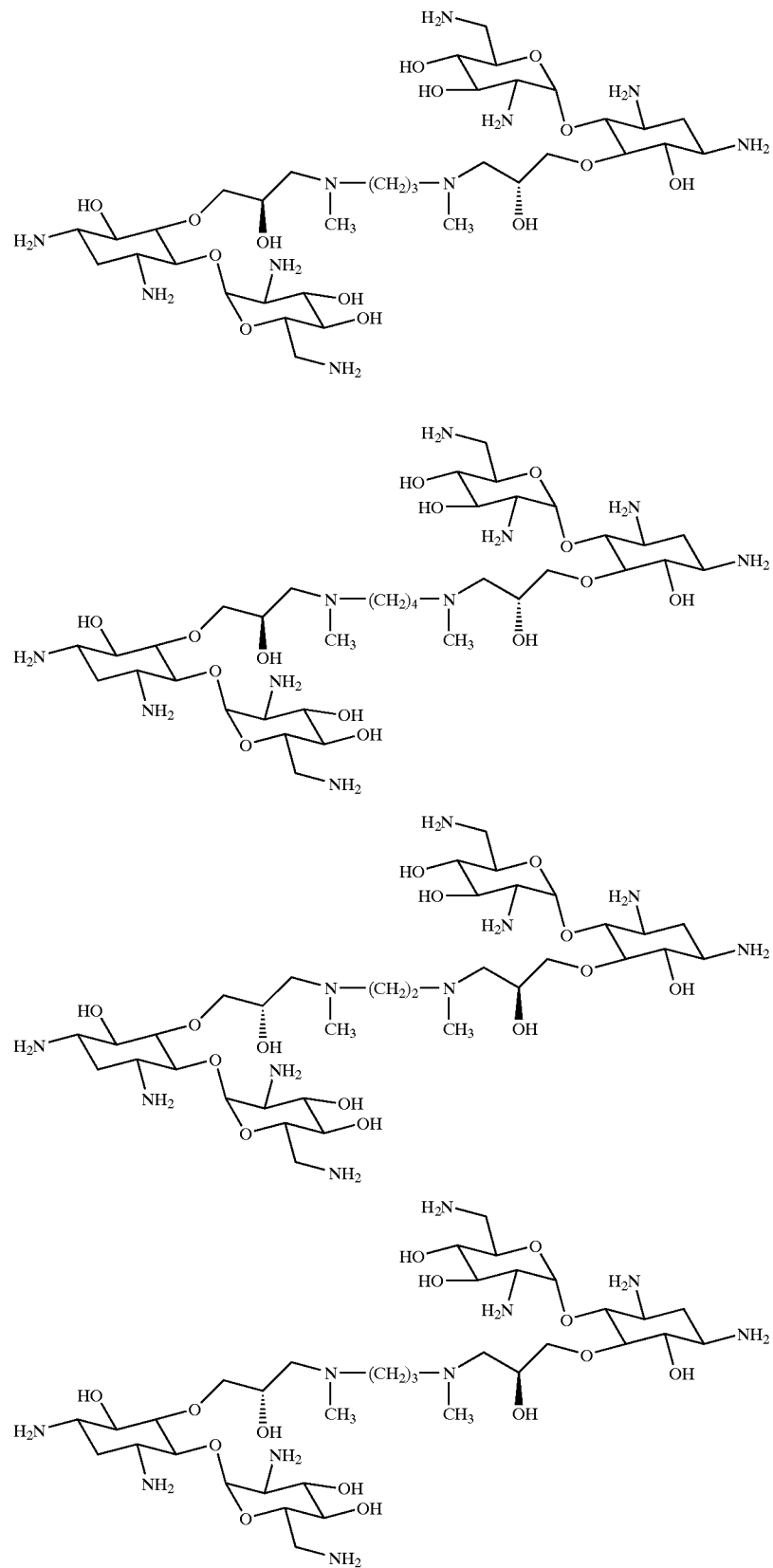

-continued

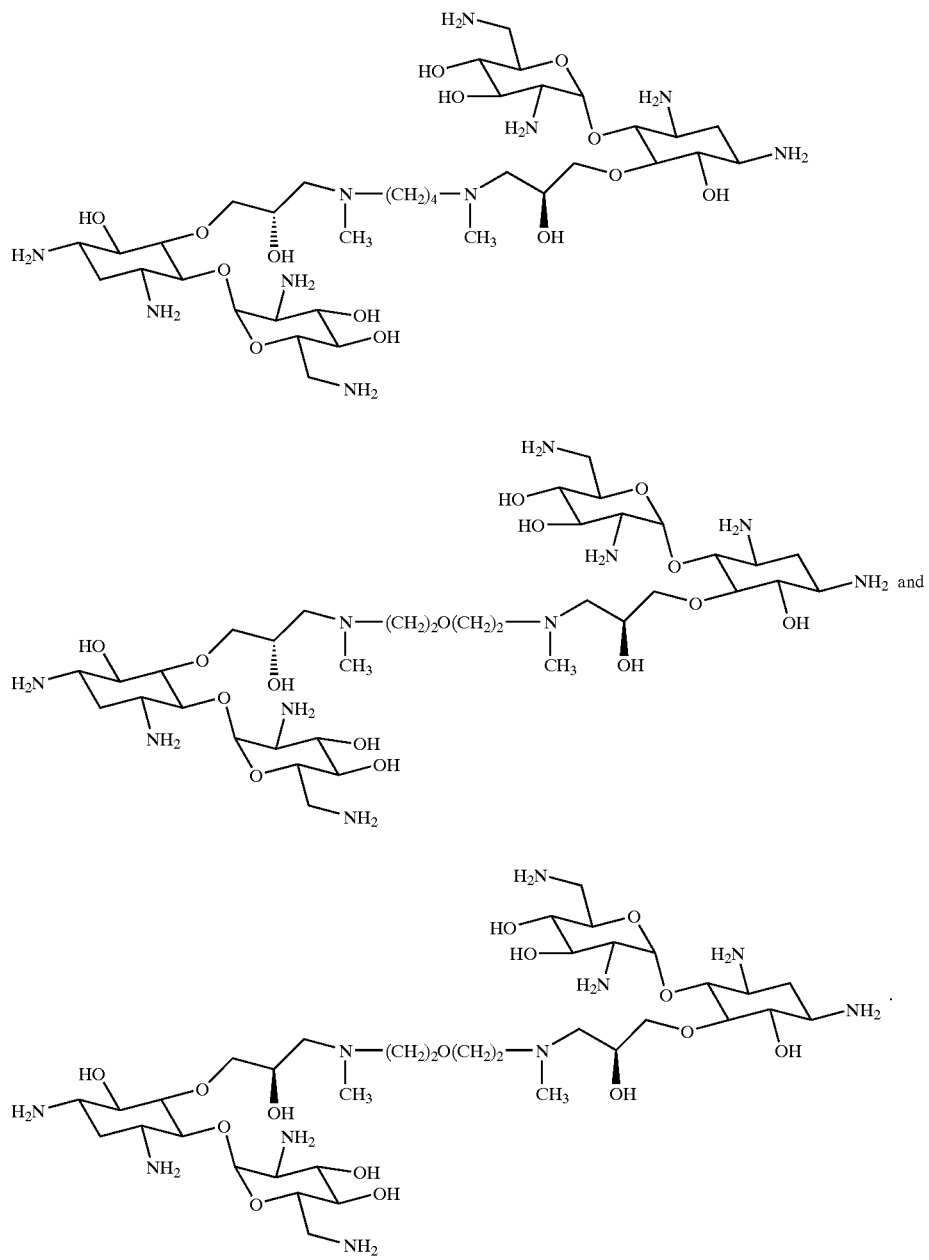

Another embodiment of the above invention is directed to a bifunctional antibiotic wherein the first and second pharmacophore are independently selected from the group consisting of neamine, neomycin B, and gentamincin $C_1$.

Another aspect of the invention is directed to a process for inhibiting translation within a bacterium having 16S rRNA with an A-site, said process comprising the step of contacting the bacterium with a concentration of any of the bifunctional antibiotics described above sufficient to inhibit translation.

Another aspect of the invention is directed to a process for simultaneously inhibiting translation and APH(2″) activity within a bacterium having both 16S rRNA with an A-site and the bifunctional enzyme AAC(6′)-APH(2″), said process comprising the step of contacting the bacterium with a concentration of any of the bifunctional antibiotics described above sufficient to inhibit translation and APH(2″) activity.

BRIEF DESCRIPTION OF FIGURES

FIG. 4 illustrates an energetic analysis of a bivalent neamine along with a cartoon drawing illustrating how dimers are likely to bind to AS-wt rRNA with high affinity.

FIG. 11 is a table giving the results of the Kirby Bauer test with known compounds and the synthesized dimers.

FIG. 12 is a table that shows the minimum inhibitory concentration (MIC, $\mu$M) in *E. Coli* ATCC 25922 and in vitro translation $IC_{50}$.

FIG. 13 shows tables of the kinetic parameters of neamine and neamine dimers for various aminoglycoside-modifying enzymes.

DETAILED DESCRIPTION

Figure 1:
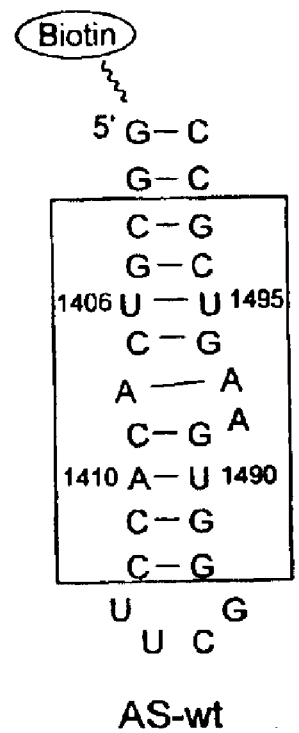
FIG. 1 illustrates the biotinylated *E. coli* 16S rRNA A-site (AS-wt) rRNA sequence.

The dissociation constant ($K_d$) and binding stoichiometry were determined using surface plasmon resonance (SPR) against an immobilized rRNA sequence modeling the A-site of prokaryotic rRNA (FIGS. 1–4) (Hendrix, M.; et al. *J. Am. Chem. Soc.* 1997, 119, 3641; Wong, C.-H.; et al. *Chem. Biol.* 1998, 5, 397). The dissociation constants were obtained from equilibrium binding curves through nonlinear curve fitting and were comparable to those obtained using Scatchard analysis. We focused on neamine as it represents the simplest effective aminoglycoside antibiotic and contains the key β-hydroxyamine motif for interaction with the phosphodiester group and the Hoogsteen face of guanine residues in RNA (FIG. 2) (Hendrix, M.; et al. *Angew. Chem., Int. Ed. Engl.* 1997, 36, 95). Neamine was found to bind biotinylated AS-wt in a 2:1 complex with a $K_d$ of 10 $\mu$M for each binding site (FIG. 3). Various dimers of neamine were therefore constructed in order to identify a bivalent aminoglycoside that would bind AS-wt with high affinity (FIG. 4), and at the same time resist and and/or inhibit the modifying enzymes due to its unnatural structure (Some aminoglycoside dimers were prepared previously; however, the monomers bind the A-site stoichiometrically: see Michael; K.; et al. *Bioorg. Med. Chem.* 1999, 7, 1361; for vancomycin dimers, see Rao, J.; Whitesides, G. H. *J. Am. Chem. Soc.* 1997, 119, 10286; Sundram, U. N.; et al. *J. Am. Chem. Soc.* 1996, 118, 13107).

Neamine dimers were prepared starting from perbenzyl perazido 5-O-carboxyethylneamine (Sucheck, S. J.; et al. *Angew. Chem., Int. Ed. Engl.* 2000, 39, 1080) (see FIG. 5), which was prepared from the 5-O-allyl precursor (Greenberg, W. A.; et al. *J. Am. Chem. Soc.* 1999, 121, 6527). Carboxyethylneamine was distributed into a Quest 210 parallel synthesizer and was activated using a cyclohexylcarbodiimide bound to macroporous polystyrene resin. Two equivalents of resin, one equivalent of acid and 0.4 equivalents of various diamine linkers were utilized to synthesize a library of neamine dimers of variable linker length. The intermediate amides were isolated by filtration and were >95% pure, as determined by NMR. The resulting dimers were first reduced under Staudinger conditions to convert the azides to amines, which were captured from solution using the resin bound sulfonic acid scavenger MP-TsOH (Argonaut). The resin was washed and the free amine was released from the resin by elution with 2 M $NH_3$ in methanol. The resulting amines were debenzylated by hydrogenolysis in the presence of 2 equivalents of acetic acid per amine. The reaction mixture was filtered, concentrated and purified by silica gel chromatography using 8:2:4:5 $NH_4OH$—$CHCl_3$-n-BuOH—EtOH, followed by cation exchange chromatography to give the pure aminoglycosides dimers 4–13. The amide-linked dimers could also be prepared via Ugi reactions, e.g. dimer 14, starting from the same perbenzyl perazido 5-O-carboxyethylneamine. This procedure is also directly applicable to parallel synthesis and could be used to increase the molecular diversity of the library.

The dimers with the highest affinity for AS-wt determined by SPR were also the most potent antibiotics, as determined by the antimicrobial assays (Greenberg, W. A.; et al. *J. Am. Chem. Soc.* 1999, 121, 6527; Phillips, I; Williams, D. In *Laboratory Methods in Antimicrobial Chemotherapy*; Gerrod, L., Ed.; Churchill Livingstone Press: Edinburg, 1978; pp 3–30) and by $IC_{50}$ of in vitro translation (Greenberg, W. A.; et al. *J. Am. Chem. Soc.* 1999, 121, 6527). Of this series, the dimers with the highest antibiotic activity, 4 and 6, showed a $K_d$ of 1.1 $\mu$M and 0.8 $\mu$M on AS-wt, respectively, ten-fold greater than neamine. Dimers with longer linker lengths had weaker affinities for AS-wt, a trend that correlated with antibiotic activity. Interestingly, all of the dimers continued to display a 2:1 binding stoichiometry, indicating that the increase in affinity is most likely due to an additional favorable (not dimeric) yet weak interaction with AS-wt. Antibiotic activities of dimers 4 and 6 were comparable to neamine, MIC=31 and 125 $\mu$M respectively, against the *E. coli* reference strain (See supplement for antibiotic testing data).

Figure 5:
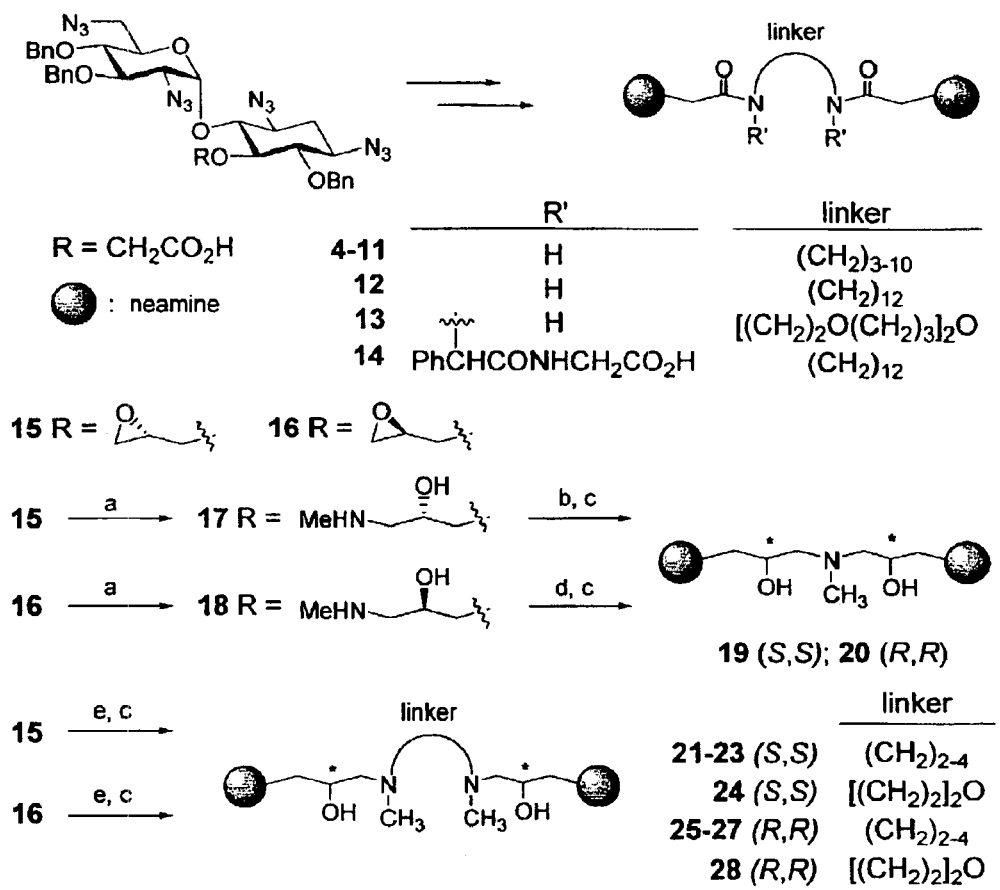
FIG. 5 illustrates a scheme that shows how the neamine dimers were prepared from a known neamine precursor.

The relatively weak antibiotic activity of these dimers led us to design a flexible and hydrophilic linker by opening the 1,2-propyloxiranes with an amine as shown in FIG. 5. The triflate of (S)-(−) and (R)-(+)-glycidol (Baldwin, J. J.; et al. *J. Med. Chem.* 1982, 25, 931; Schlecker, R.; Thieme, P. C. *Tetrahedron* 1988, 44, 3289) was used to alkylate perbenzyl perazido neamine to form epoxides 15 and 16, respectively. Epoxides 15 and 16 were heated for 16 h in a sealed tube with excess methylamine to form 1,2-hydroxy amines 17 and 18, respectively. These hydroxy amines could then be used in an addition reaction with another equivalent of epoxide 15 or 16 to form dimers 19 and 20, respectively, after deprotection. Epoxides 15 and 16 were also opened with 0.5 equivalents of a N,N'-methyldiamines to afford protected dimers 21–28. N,N'-methyldiamine that were not commercially available were readily prepared by a one-pot synthesis via imine formation with a primary diamine and benzaldehyde, alkylation of the intermediate imime with dimethyl sulfate followed by hydrolysis of the alkylimine afforded N,N'-methyldiamines in high yield (Devinsky, F.; et al. *Synthesis* 1980, 4, 303). The resulting dimers were deprotected as previously described to afford dimers 21–28. These dimers possessed significantly increased antibiotic activity compared to the amide-linked dimers. Antibiotic activity was greatest with the diaminobutane linker in dimer 27, which showed a MIC=6.25 $\mu$M against *E. coli* and $K_d$=40 nM (AS-wt) with 1 to 1 stoichiometry (Compound 27 is also effective against other strains, including *P. aeruginosa* ATCC 27853, *P. aeruginosa*, PAO-1, *S. aureus* ATCC 29213 and ATCC 33591-MRSA, and *E. faecalis* ATCC 29212 and is 3 times more effective than tobramycin against the tobramycin-resistant strain of P. aeruginosa from cystic fibrosis patients.).

To better understand the relationship between RNA binding and antibiotic activity, inhibition of in vitro translation of luciferase gene (Greenberg, W. A.; et al. J. Am. Chem. Soc. 1999, 121, 6527) was measured as a function of MIC, FIG. 6. This analysis was used to validate the target and characterize potential transport limitations for the aminoglycosides, and in vitro translation inhibition is expected to be a better indicator of aminoglycoside selectivity for 16S rRNA compared to binding affinity measurements with the A-site sequences (Hendrix, M.; et al. J. Am. Chem. Soc. 1997, 119, 3641; Wong, C.-H.; et al. Chem. Biol. 1998, 5, 397; Greenberg, W. A.; et al. J. Am. Chem. Soc. 1999, 121, 6527). A nearly linear relationship between the $IC_{50}$ of translation inhibition and the MIC was observed. This analysis is useful for analyzing structure activity relationships within a similar series of compounds. Compounds falling below the line in FIG. 6 may suffer from transport limitation while compounds above the line may act via a fundamentally different mode of action than compounds at or near the line.

Further study of neamime dimers 4, 6 and 27 using several aminoglycoside-modifying enzymes revealed that the dimers were poor substrates for AAC(6')-Ii and APH(3')-IIIa, responsible for 6'- and 3'-N-acetylation and O-phosphorylation, respectively (Wright, G. D.; et al. Adv. Exp. Med. Biol. 1998, 456, 27; Kondo, S.; Hotta, K. J. Infect. Chemother. 1999, 5, 1; Mingeot-Leclerco, M.-P.; et al. Antimicrob. Agents Chemother. 1999, 43, 727). In addition, dimers 4, 6 and 27 were poor substrates for the AAC(6') activity of the bifunctional aminoglycoside modifying-enzyme AAC(6')-APH(2") (Wright, G. D.; et al. Adv. Exp. Med. Biol. 1998, 456, 27; Kondo, S.; Hotta, K. J. Infec. Chemother. 1999, 5, 1; Mingeot-Leclerco, M.-P.; et al. Antimicrob. Agents Chemother. 1999, 43, 727; Daigle, D. M.; et al. Chem. Biol. 1999, 6, 99; Azucena, E.; et al. J. Am. Chem. Soc. 1997, 119, 2317; Patterson, J.-E.; Zervos, M. J. Rev. Infect. Dis. 1990, 12, 644), and not substrates for the APH(2") activity of MC(6')-APH(2"). They were in fact potent competitive inhibitors of the APH(2") activity, $K_{is}$= 0.8 μM for dimer 4, 0.1 μM for 6 and 0.7 μM for 27.

DETAILED DESCRIPTION OF FIGURES

FIG. 1 shows the biotinylated E. coli 16S rRNA A-site (AS-wt) rRNA sequence.
It is this portion of the bacterial RNA on the 16S domain of the ribosome which is bound by the aminoglycosides. This interferes with translational fidelity during protein synthesis.

Figure 2:
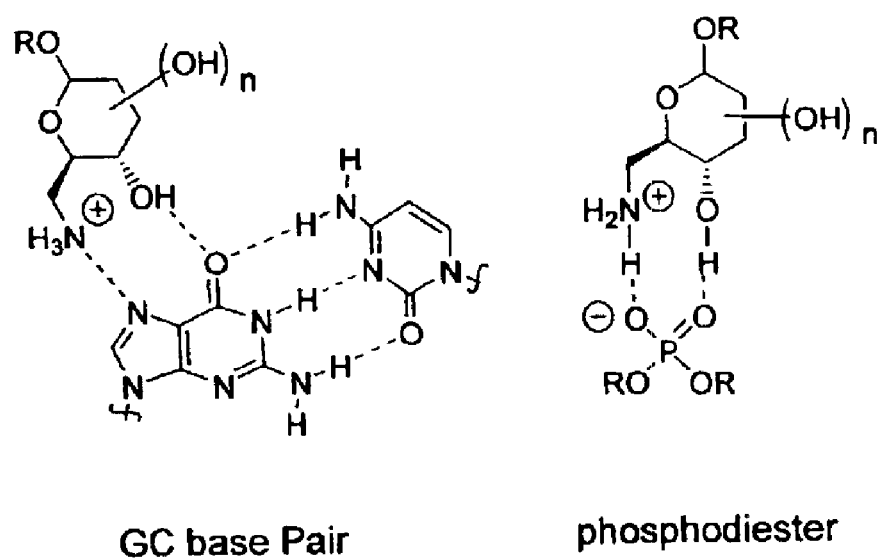
FIG. 2 illustrates the mode of action of β-hydroxyamine commonly found in aminoglycoside antibiotics.
Figure 3:
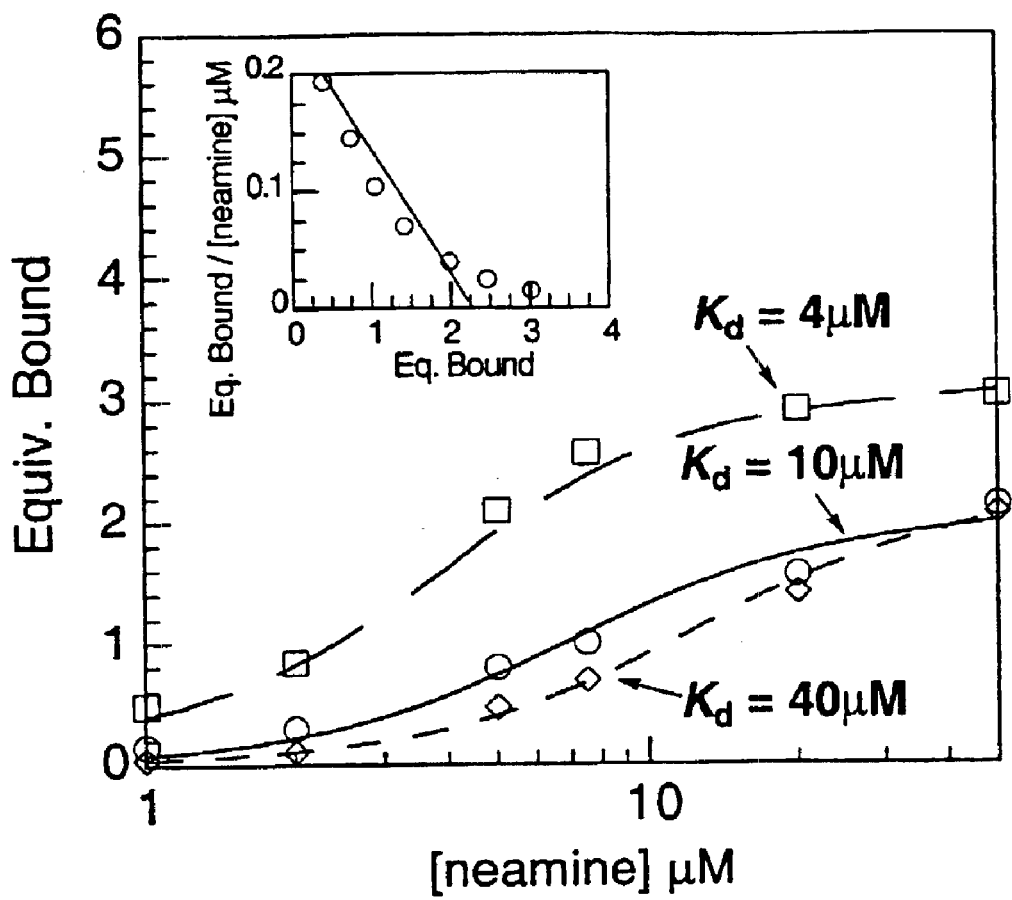
FIG. 3 illustrates is a graph showing a binding isotherm of neamine binding to AS-wt (circles) and control mutants (U1406A, squares; U1485A, diamonds) for determination of dissociation constants ($K_d$=inverse slope) and binding stoichiometry (x-intercept).

FIG. 2 shows the mode of action of β-hydroxyamine commonly found in aminoglycoside antibiotics. The β-hydroxyamine motif interacts not only with the phosphodiester group but also the Hoogsteen face of guanine residues in RNA.

FIG. 3 is a graph showing a binding isotherm of neamine binding to AS-wt (circles) and control mutants (U1406A, squares; U1485A, diamonds) for determination of dissociation constants ($K_d$=inverse slope) and binding stoichiometry (x-intercept). The binding is sequence selective. The inset in the figure is a Scatchard plot which shows the binding stoichiometry.

FIG. 4 is an energetic analysis of a bivalent neamine along with a cartoon drawing illustrating how dimers are likely to bind to AS-wt rRNA with high affinity. Neamine units bind to AS-wt with a $K_d$ of 10 μM per binding site. Addition of the proper linker would enable the unnatural dimer to bind with much higher affinity and resist modifying enzymes because of its unnatural structure.

FIG. 5 is a scheme that shows how the neamine dimers were prepared from a known neamine precursor. The starting material is perbenzyl perazido 5-O-carboxyethylneamine which is prepared from the 5-O-allyl precursor. A variety of diamines were chosen to form a diamide linker to the neamine units. Dimer 14 was synthesized using the Ugi reaction. Four separate components are added during this synthetic procedure. Synthetic steps from the neamine expoxides are shown at the bottom of the scheme. Simple nucleophilic opening of the epoxide ring generates the dimers from a primary amine or a primary diamine precursor.

Figure 6:
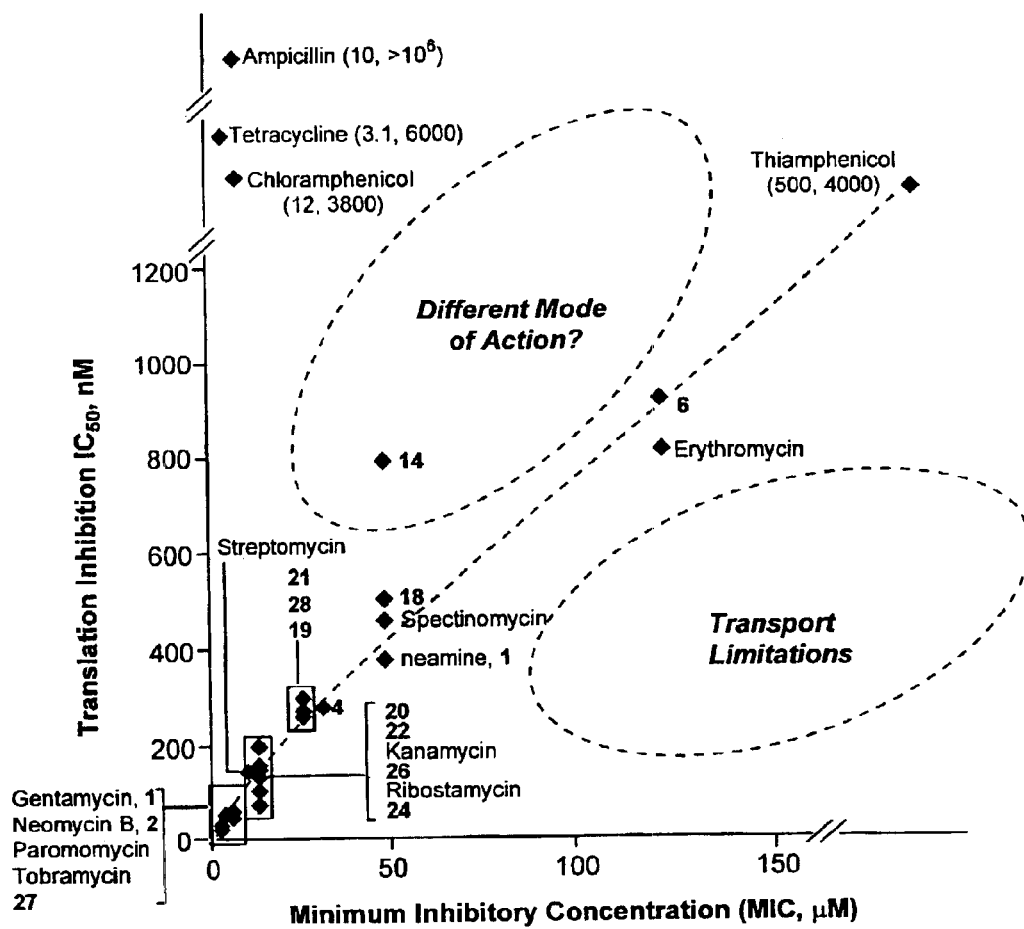
FIG. 6 illustrates a graph which demonstrates the relationship between antibiotic activity (MIC, minimum inhibitory concentration) and translation inhibition ($IC_{50}$).

FIG. 6 is a graph which demonstrates the relationship between antibiotic activity (MIC, minimum inhibitory concentration) and translation inhibition ($IC_{50}$). The compounds above the line do not target RNA and have different modes of antibiotic action, while those to the right of the line exhibit transport limitations. What was measured is the inhibition of in vitro translation of the luciferase gene measured as a function of MIC. This analysis was used to validate the target and characterize potential transport limitations for the aminoglycosides, and in vitro translation inhibition is expected to be a better indicator of aminoglycoside selectivity for 16S rRNA compared to binding affinity measurements with the A-site sequences. A nearly linear relationship between $IC_{50}$ of translation inhibition and the MIC was observed.

Figure 7:
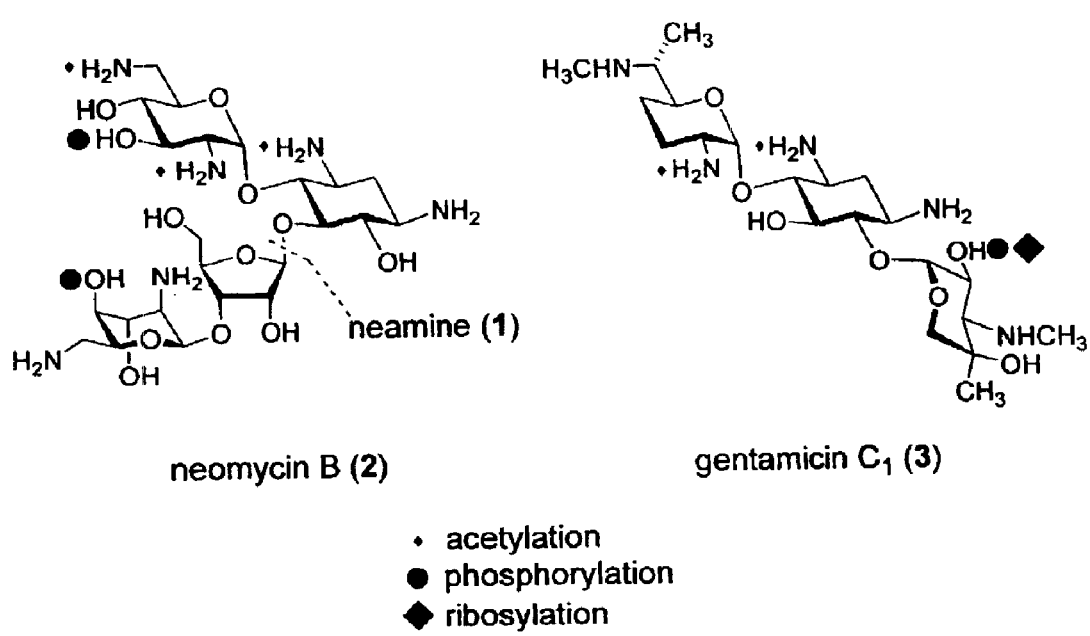
FIG. 7 illustrates the sites of enzymatic modification on neomycin B and gentamicin $C_1$.

FIG. 7 shows the sites of enzymatic modification on neomycin B and gentamicin $C_1$. N-acetylation, phosphorylation and O-ribosylation are the major modifications catalyzed by resistance causing enzymes.

Figure 8:
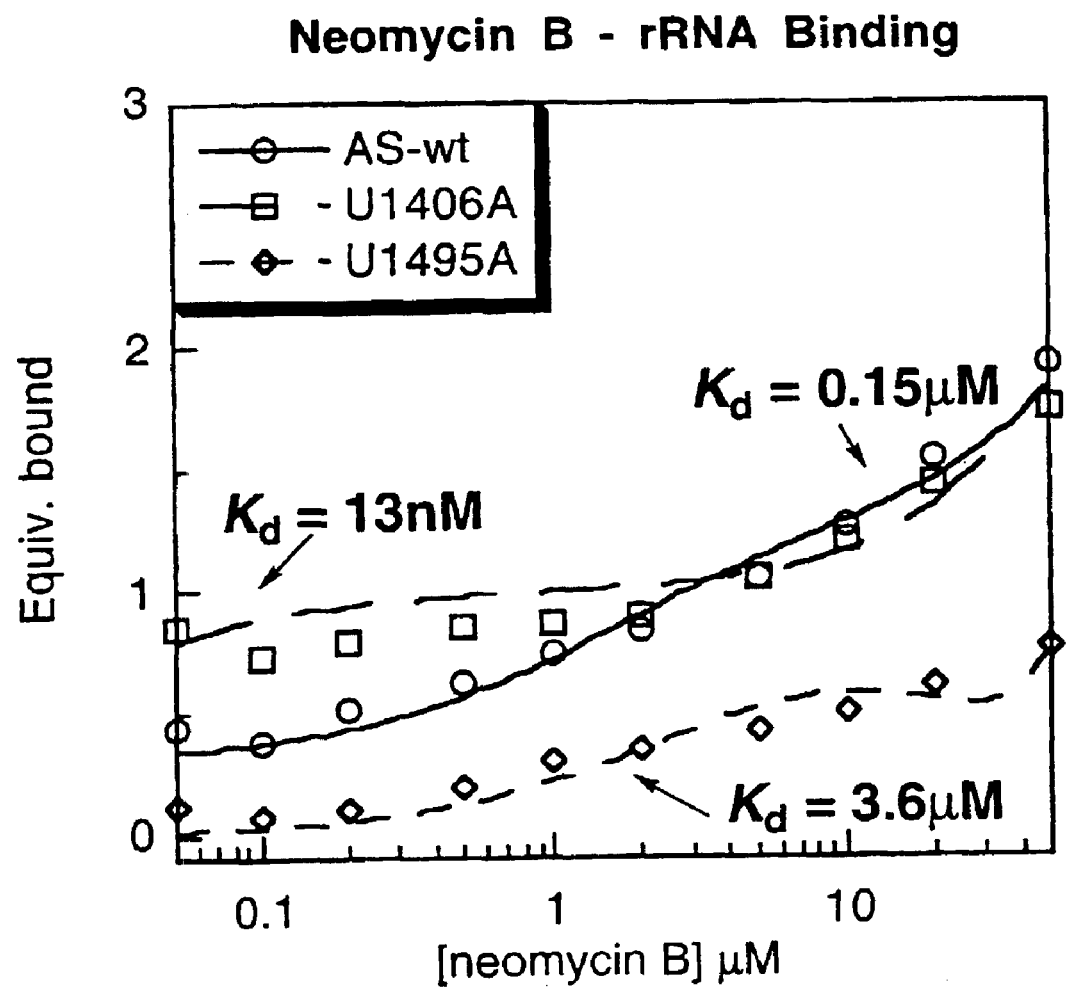
FIG. 8 illustrates a graph showing the results of surface plasmon resonance experiments on neomycin B binding to AS-wt rRNA and mutants.

FIG. 8 is a graph showing the results of surface plasmon resonance experiments on neomycin B binding to AS-wt rRNA and mutants. The circles are for the wild type organism and the squares and diamonds are for the two different mutants. The binding is sequence selective.

Figure 9:
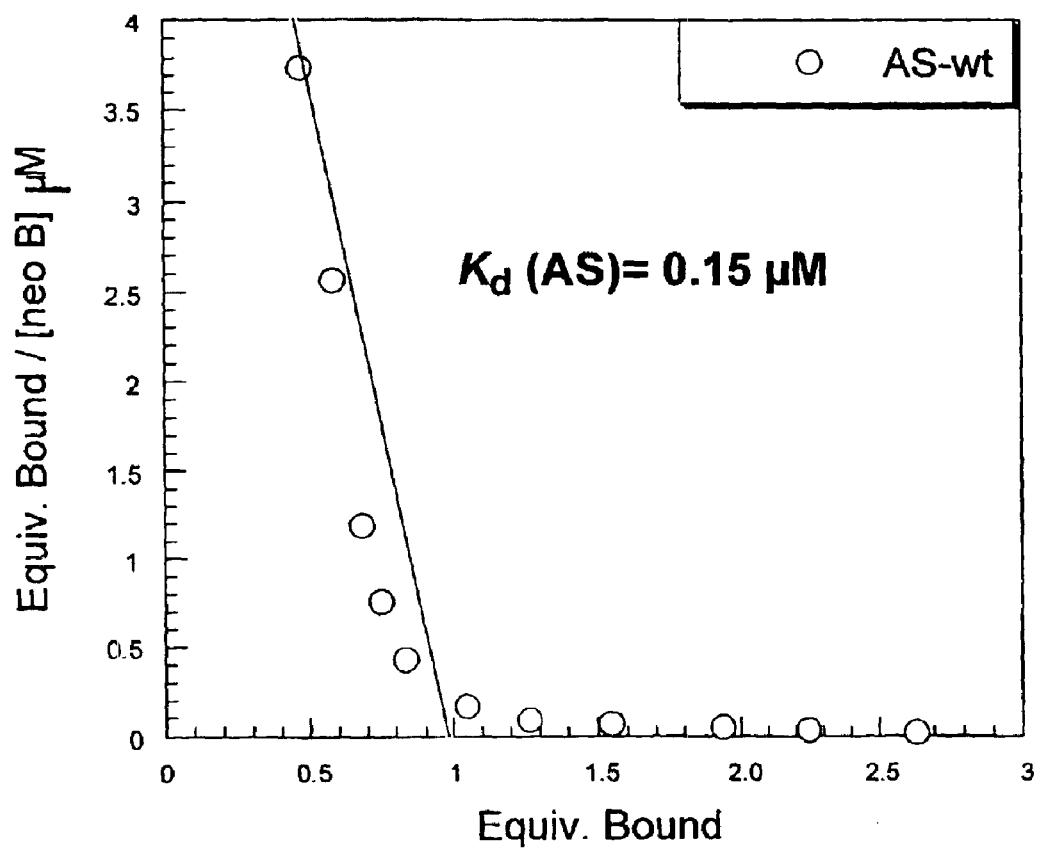
FIG. 9 illustrates a Scatchard plot for determining dissociation constants ($K_d$, inverse slope and binding stoichiometry (x-intercept) for the wild type organism.

FIG. 9 is a Scatchard plot for determining dissociation constants ($K_d$, inverse slope and binding stoichiometry (x-intercept) for the wild type organism. The binding is sequence selective.

Figure 10:
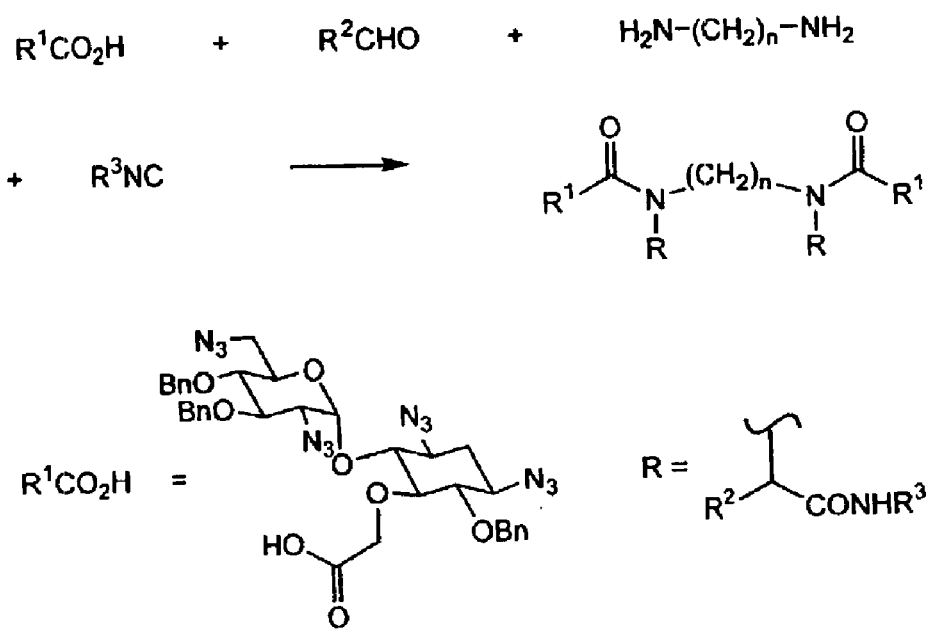
FIG. 10 illustrates an Ugi reaction where four separate components are reacted to produce an amide-linked dimer.

FIG. 10 shows an Ugi reaction where four separate components are reacted to produce an amide linked dimer. Compound 14 was synthesized in this reaction to give a linked dimer. 5-Ethylcarboxyl-1,3,2',6'-tetraazido-6,3',4'-tri-O-benzyl-neamine (60 mg, 79 μmol), methyl isocyanoacetate (36 μL, 397 μmol), benzaldehyde (8 μL, 79 μmol), and diaminododecane (8 mg, 40 μmol) were dissolved in a mixture of anhydrous $CH_2Cl_2$/methanol (1:1, 800 μl). After stirring 48 hours at ambient temperature, the reaction was diluted with ethyl acetate (5 ml). It was then washed with 1M HCl (2×5 ml), saturated sodium bicarbonate (2×5 ml), and brine (1×5 ml). The aqueous extracts were re-extracted with ethyl acetate (2×5 ml). The combined organic extracts were dried ($Na_2SO_4$), filtered, and concentrated. Flash chromatography (silica gel, gradient hexane to 1:1 hexane/ethyl acetate) yielded protected neamine dimer 14 (21.7 mg, 26%).

FIG. 11 is a table giving the results of the Kirby Bauer test with known compounds and the synthesized dimers. The numbers under the test strains are for diameters (mm) of zones of inhibition. All compounds except neomycin and gentamicin were spotted at 200 nmoles/disk; neomycin was spotted at 33 nmoles/disk (30 μg) while gentamicin was spotted at 10 nmole/disk (10 μg). Surface plasmon resonance $K_d$ values for dimers 4–13 is also provided.

FIG. 12 is a table that shows the minimum inhibitory concentration (MIC, μM) in E. Coli ATCC 25922 and in vitro translation $IC_{50}$. The data from this table is graphed in FIG. 6 and shows the likely mechanism of action for the antibiotics.

FIG. 13 shows tables of the kinetic parameters of neamine and neamine dimers for various aminoglycoside-modifying enzymes. BF refers to the bifunctional enzyme AAC(6')-APH(2"), where the particular activity is indicated. The neamine data were obtained from Daigle, D. M.; et al. *Chem. Biol.* 1999, 6, 99.

Experimental Section

Reactions were performed under inert atmosphere unless otherwise stated. THF and $CH_2Cl_2$ were distilled under Ar with benzophenone ketyl and $CaH_2$, respectively. NMR spectra were obtained on a Bruker AMX-400. The sites of enzymatic modification of neomycin and gentamicin that cause drug resistance are shown in FIG. 1 (Daigle, D. M.; et al. *Chem. Biol.* 1999, 6, 99). Synthesis of biotinylated RNAs and surface plasmon resonance experiments were performed as previously described and $K_d$ values were also calculated as previously described (FIG. 2) (Hendrix, M.; et al. *J. Am. Chem. Soc.* 1997, 119, 3641).

Antimicrobial Testing: The Kirby-Bauer Disk assay was performed as previously described (Hendrix, M.; et al. *J. Am. Chem. Soc.* 1997, 119, 3641; Phillips, I.; Williams, D. In *Laboratory Methods in Antimicrobial Chemotherapy*; Gerrod, L., Ed.; Churchill Livingstone Press: Edinburg, 1978; pp 3–30). Reference strains *E. coli* ATCC 25922 and *S. aureus* ATCC 25923 were obtained as lyophilized pellets (Difco). MIC testing was performed as recommended in the NCCLS Publication M7-A4.

In vitro translation assays: A coupled transcription-translation assay was performed as previously described with luciferase DNA to determine the extent of translational inhibition in the presence of the various aminoglycosides/mimetics (Greenberg, W. A.; et al. *J. Am. Chem. Soc.* 1999, 121, 6527). The transcription/translation mixture, or S-30 extract, and the reaction buffers were prepared as described previously with slight modifications (Greenberg, W. A.; et al. *J. Am. Chem. Soc.* 1999, 121, 6527). The translation assays were performed by mixing all of the reagents, various amounts of the compounds to be tested, and the DNA template into a small, RNase-free microcentrifuge tube. The final addition was always S-30 extract, and the reaction was maintained at 21°+/−1° C. in a water bath. The reaction was terminated after 30 minutes by diluting the reaction 10-fold with a luciferase dilution buffer containing 1% Triton X-100. Translation yield was determined by mixing 1 $\mu L$ of the diluted reaction mixture with 50 $\mu L$ of luciferase assay reagent (20 mM Tricine, pH 7.8; 15 mM $MgSO_4$; 0.1 mM EDTA; 33.3 mM DTT; 270 $\mu M$ coenzyme A; 470 $\mu M$ luciferin; and 530 $\mu M$ ATP) and monitoring the luminescence with a Turner Designs luminometer. For each assay, points were collected in duplicate, and the full assays were performed at least three times.

5-Ethylcarboxyl-1,3,2',6'-tetraazido-6,3',4'-tri-O-benzylneamine. (Sucheck, S. J.; et al. *Angew. Chem., Int. Ed. Engl.* 2000, 39, 1080) 5-O-Allyl -1,3,2',6'-tetraazido-6,3',4'-tri-O-benzylneamine (Greenberg, W. A.; et al. *J. Am. Chem. Soc.* 1999, 121, 6527) (264 mg, 0.340 mmol) was dissolved in 14 mL of 1:1 methanol-dichloromethane and was cooled to −78° C. Ozone was bubbled through the solution until it became light blue in color. The solution was treated with 272 $\mu L$ of dimethyl sulfide and was allowed to stir one hour while it warmed to room temperature. The solvents were removed under diminished pressure and the crude aldehyde was taken up in 6 mL of 1:1 carbon tetrachloride-acetic acid. The solution was cooled to 0° C. in an ice bath and 305 mg of sodium chlorite (3.39 mmol) was added in portions over 1 h. The solution was poured into an ice cold $Na_2S_2O_5$ solution, acidified to pH 1 with 0.5 N $H_2SO_4$, extracted with five 50-mL portions ethyl acetate and dried ($MgSO_4$). The solution was concentrated by co-evaporation with toluene under diminished pressure. The product was purified by silica gel flash column chromatography (3×15 cm). Elution with 2:1+1% hexanes-ethyl acetate-acetic acid afforded the carboxylic acid as a colorless foam: yield 205 mg (80%); silica gel TLC $R_f$ 0.56 (1:1+1% hexanes-ethyl acetate-acetic acid); mass spectrum (FAB), m/z 887.1961 (M+Cs)$^+$ ($C_{35}H_{38}N_{12}O_8Cs$ requires 887.1990).

General Procedure for the Synthesis of Neamine Dimers. 5-Ethylcarboxyl-1,3,2',6'-tetraazido-6,3',4'-tri-O-benzylneamine (0.0826 mmol/tube) was dissolved in 1.5 mL/tube of dry dichloromethane and was distributed into a Quest 210 parallel synthesizer (Argonaut Technologies; San Carlos, Calif.). To each tube was added 143 mg of MP-carbodiimide resin (1.15 mmol/g) (Argonaut Technologies; San Carlos, Calif.) followed by the diamine (0.0413 mmol/tube). The solutions were agitated for 16 hours, filtered and concentrated under diminished pressure to obtain the dimers as colorless foams.

N,N'-1,3-bis(5-Ethylcarboxyl-1,3,2',6'-tetraazido-6,3',4'-tri-O-benzylneamine)-propylamide, Protected Dimer 4. Yield: 16.9 mg (26%); silica gel TLC $R_f$ 0.54 (1:1 hexanes-ethyl acetate); mass spectrum (MALDI-FTMS), m/z 1569.6495 (M+Na)$^+$ ($C_{73}H_{82}N_{26}O_{14}Na$ requires 1569.6401).

N,N'-1,3-bis(5-Ethylcarboxyl-1,3,2',6'-tetraazido-6,3',4'-tri-O-benzylneamine)butyl-amide, Protected Dimer 5. Yield: 25.9 mg (40%); silica gel TLC $R_f$ 0.54 (1:1 hexanes-ethyl acetate); mass spectrum (MALDI-FTMS), m/z 1583.6550 (M+Na)$^+$ ($C_{74}H_{84}N_{26}O_{14}Na$ requires 1583.6558).

N,N'-1,3-bis(5-Ethylcarboxyl-1,3,2',6'-tetraazido-6,3',4'-tri-O-benzylneamine)-pentylamide, Protected Dimer 6. Yield: 33.1 mg (51%); silica gel TLC $R_f$ 0.54 (1:1 hexanes-ethyl acetate); mass spectrum (MALDI-FTMS), m/z 1597.6744 (M+Na)$^+$ ($C_{75}H_{86}N_{26}O_{14}Na$ requires 1597.6714).

N,N'-1,3-bis(5-Ethylcarboxyl-1,3,2',6'-tetraazido-6,3',4'-tri-O-benzylneamine)-hexylamide, Protected Dimer 7. Yield: 25.8 mg (39%); silica gel TLC $R_f$ 0.54 (1:1 hexanes-ethyl acetate); mass spectrum (MALDI-FTMS), m/z 1611.6886 (M+Na)$^+$ ($C_{76}H_{88}N_{26}O_{14}Na$ requires 1611.6871).

N,N'-1,3-bis(5-Ethylcarboxyl-1,3,2',6'-tetraazido-6,3',4'-tri-O-benzylneamine)-heptylamide, Protected Dimer 8. Yield: 39.6 mg (60%); silica gel TLC $R_f$ 0.54 (1:1 hexanes-ethyl acetate); mass spectrum (MALDI-FTMS), m/z 1625.7021 (M+Na)$^+$ ($C_{77}H_{90}N_{26}O_{14}Na$ requires 1625.7027).

N,N'-1,3-bis(5-Ethylcarboxyl-1,3,2',6'-tetraazido-6,3',4'-tri-O-benzylneamine)-octylamide, Protected Dimer 9. Yield: 31.7 mg (47%); silica gel TLC $R_f$ 0.54 (1:1 hexanes-ethyl acetate); mass spectrum (MALDI-FTMS), m/z 1639.7137 (M+Na)$^+$ ($C_{78}H_{12}N_{26}O_{14}Na$ requires 1639.7184).

N,N'-1,3-bis(5-Ethylcarboxyl-1,3,2',6'-tetraazido-6,3',4'-tri-O-benzylneamine)-nonylamide, Protected Dimer 10. Yield: 29.4 mg (44%); silica gel TLC $R_f$ 0.59 (1:1 hexanes-ethyl acetate); mass spectrum (MALDI-FTMS), m/z 1653.7423 (M+Na)$^+$ ($C_{79}H_{94}N_{26}O_{14}Na$ requires 1653.7340).

N,N'-1,3-bis(5-Ethylcarboxyl-1,3,2',6'-tetraazido-6,3',4'-tri-O-benzylneamine)decyl-amide, Protected Dimer11. Yield: 36.7 mg (54%); silica gel TLC $R_f$ 0.63 (1:1 hexanes-ethyl acetate); mass spectrum (MALDI-FTMS), m/z 1667.7483 (M+Na)$^+$ (C$_{80}$H$_{96}$N$_{26}$O$_{14}$Na requires 1667.7497).

N,N'-1,3-bis(5-Ethylcarboxyl-1,3,2',6'-tetraazido-6,3',4'-tri-O-benzylneamine)-dodecylamide, Protected Dimer 12. Yield: 34.2 mg (50%); silica gel TLC R$_f$ 0.65 (1:1 hexanes-ethyl acetate); mass spectrum (MALDI-FTMS), m/z 1695.7802 (M+Na)$^+$ (C$_{82}$H$_{100}$N$_{26}$O$_{14}$Na requires 1695.7810).

N,N'-1,3-bis(5-Ethylcarboxyl-1,3,2',6'-tetraazido-6,3',4'-tri-O-benzylneamine)-4,7,10-trioxotetradecylamide, Protected Dimer 13. Yield: 32.5 mg (47%); silica gel TLC R$_f$ 0.26 (1:1 hexanes-ethyl acetate); mass spectrum (MALDI-FTMS), m/z 1715.7432 (M+Na)$^+$ (C$_{80}$H$_{96}$N$_{26}$O$_{17}$Na requires 1715.7344).

General Procedure for the Azide Reduction of Neamine Dimers. The N,N'-bis(5-ethyl-carboxyl-1,3,2',6'-tetraazido-6,3',4'-tri-O-benzylneamine)alkylamides were dissolved in 1.5 mL/tube of dry THF and were distributed into a Quest 210 parallel synthesizer. To each tube was added 150 μL of water followed by 15 μL of 1 N NaOH solution. To the resulting solutions were added 10 equivalents of 1 M trimethylphosphine in THF for each tube. The solutions were agitated for 16 hours and 100 mg/tube of MP-TsOH resin (1.32 mmol/g) (Argonaut Technolo-gies; San Carlos, Calif.) was added. The solutions were allowed to agitate for 2 hours and were washed with three 10-mL portions of methanol. The resin bound amines were released from the resin by washing the resin with two 5-mL portions of 2 N ammonia in methanol. The solutions were concentrated under diminished pressure to obtain the amines as light yellow syrups. The amines were subjected to hydrogenolysis conditions without further characterization.

General Procedure for the Hydrogenolysis of Neamine Dimers. The N,N'-bis(5-ethyl-carboxyl-6,3',4'-tri-O-benzylneamine)alkylamides were dissolved in 1 mL/vial of glacial acetic acid. To each vial was added 50 μg of 20% Pd(OH)$_2$/C (Degussa type) and the solutions were placed under 1 atm of H$_2$. The solutions were stirred for 16 hours and were concentrated under diminished pressure. The deprotected dimers were purified by flash chromatography on silica gel (1×15 cm). Elution with 8:2:5:4 30% ammonium hydroxide-chloroform-ethanol-butanol afforded the dimers as a colorless glasses. The dimers were resuspended in water and applied to Dowex 50WX4-50 H$^+$ and washed with 5 mL of water. The dimers were eluted with 3% ammonium hydroxide to obtain the dimers as colorless foams after lyophilization.

N,N'-1,3-bis(5-Ethylcarboxyl-neamine)propylamide (4). Yield: 0.9 mg (10%); silica gel TLC R$_f$ 0.32 (8:2:5:4 30% ammonium hydroxide-chloroform-ethanol-butanol); mass spectrum (MALDI-FTMS), m/z 821.4355 (M+Na)$^+$ (C$_{31}$H$_{62}$N$_{10}$O$_{14}$Na requires 821.4345).

N,N'-1,3-bis(5-Ethylcarboxyl-neamine)butylamide (5). Yield: 1.4 mg (10%); silica gel TLC R$_f$ 0.32 (8:2:5:4 30% ammonium hydroxide-chloroform-ethanol-butanol); mass spectrum (MALDI-FTMS), m/z 835.0000 (M+Na)$^+$ (C$_{32}$H$_{64}$N$_{10}$O$_{14}$Na requires 835.4501).

N,N'-1,3-bis(5-Ethylcarboxyl-neamine)pentylamide (6). Yield: 0.9 mg (5.2%); silica gel TLC R$_f$ 0.32 (8:2:5:4 30% ammonium hydroxide-chloroform-ethanol-butanol); mass spectrum (MALDI-FTMS), m/z 849.4668 (M+Na)$^+$ (C$_{33}$H$_{66}$N$_{10}$O$_{14}$Na requires 849.4658).

N,N'-1,3-bis(5-Ethylcarboxyl-neamine)hexylamide (7). Yield: 1.4 mg (10%); silica gel TLC R$_f$ 0.37 (8:2:5:4 30% ammonium hydroxide-chloroform-ethanol-butanol); mass spectrum (MALDI-FTMS), m/z 863.4838 (M+Na)$^+$ (C$_{34}$H$_{68}$N$_{10}$O$_{14}$Na requires 863.4814).

N,N'-1,3-bis(5-Ethylcarboxyl-neamine)heptylamide (8). Yield: 1.7 mg (8.1%); silica gel TLC R$_f$ 0.37 (8:2:5:4 30% ammonium hydroxide-chloroform-ethanol-butanol); mass spectrum (MALDI-FTMS), m/z 855.5173 (M+H)$^+$ (C$_{35}$H$_{71}$N$_{10}$O$_{14}$ requires 855.5151).

N,N'-1,3-bis(5-Ethylcarboxyl-neamine)octylamide (9). Yield: 4.4 mg (26%); silica gel TLC R$_f$ 0.58 (8:2:5:4 30% ammonium hydroxide-chloroform-ethanol-butanol); mass spectrum (MALDI-FTMS), m/z 891.5131 (M+Na)$^+$ (C$_{36}$H$_{72}$N$_{10}$O$_{14}$Na requires 891.5127).

N,N'-1,3-bis(5-Ethylcarboxyl-neamine)nonylamide (10). Yield: 2.4 mg (15%); silica gel TLC R$_f$ 0.74 (8:2:5:4 30% ammonium hydroxide-chloroform-ethanol-butanol); mass spectrum (MALDI-FTMS), m/z 883.5472 (M+H)$^+$ (C$_{37}$H$_{75}$N$_{10}$O$_{14}$ requires 883.5464).

N,N'-1,3-bis(5-Ethylcarboxyl-neamine)decylamide (11). Yield: 13 mg (13%); silica gel TLC R$_f$ 0.74 (8:2:5:4 30% ammonium hydroxide-chloroform-ethanol-butanol); mass spectrum (MALDI-FTMS), m/z 897.5583 (M+H)$^+$ (C$_{38}$H$_{77}$N$_{10}$O$_{14}$ requires 897.5621).

N,N'-1,3-bis(5-Ethylcarboxyl-neamine)dodecylamide (12). Yield: 0.7 mg (3.7%); silica gel TLC R$_f$ 0.79 (8:2:5:4 30% ammonium hydroxide-chloroform-ethanol-butanol); mass spectrum (MALDI-FTMS), m/z 947.5729 (M+Na)$^+$ (C$_{40}$H$_{80}$N$_{10}$O$_{14}$Na requires 947.5753).

N,N'-1,3-bis(5-Ethylcarboxyl-neamine)-4,7,10-trioxotetradecylamide (13). Yield: 2.2 mg (12%); silica gel TLC R$_f$ 0.79 (8:2:5:4 30% ammonium hydroxide-chloroform-ethanol-butanol); mass spectrum (MALDI-FTMS), m/z 1715.7432 (M+Na)$^+$ (C$_{38}$H$_{76}$N$_{10}$O$_{17}$Na requires 1715.7344).

Protected Neamine Dimer 14. For a schematic Ugi reaction, see FIG. 3. In a representative example, 5-Ethylcarboxyl-1,3,2',6'-tetraazido-6,3',4'-tri-O-benzylneamine neamine (60 μg, 79 μmol), methyl isocyanoacetate (36 μL, 397 μmol), benzaldehyde (8 μL, 79 μmol), and diaminododecane (8 mg, 40 μmol) were dissolved in a mixture of anhydrous CH$_2$Cl$_2$/methanol (1:1, 800 μl). After stirring 48 hours at ambient temperature, the reaction was diluted with ethyl acetate (5 ml). It was then washed with 1M HCl (2×5 ml), saturated sodium bicarbonate (2×5 ml), and brine (1×5 ml). The aqueous extracts were re-extracted with ethyl acetate (2×5 ml). The combined organic extracts were dried (Na$_2$SO$_4$), filtered, and concentrated. Flash chromatography (silica gel, gradient hexane to 1:1 hexane/ethyl acetate) yielded protected neamine dimer 14 (21.7 mg, 26%). HRMS (FAB) calcd for C$_{104}$H$_{122}$N$_{28}$O$_{20}$ (M+Cs)$^+$ 2215.8445, found 2215.8587.

Neamine Dimer 14. Protected neamine dimer 14 (21.4 mg, 10 μmol) was suspended in ethanol (250 μl). Anhydrous hydrazine (3.2 μl, 100 μmol) was added, followed by Raney nickel (~10 mg) that had been washed thoroughly with ethanol. The reaction was stirred overnight at ambient temperature, then filtered through a plug of Celite and concentrated. The resulting residue was dissolved in H$_2$O/AcOH (1:1, 0.04 M). Pd(OH)$_2$/C (~10 mg, Degussa type) was added and the reaction stirred under a H$_2$ atmosphere (balloon) overnight. The reaction was filtered through a plug of Celite and lyophilized. Purification was accomplished on CG-50 cation exchange resin, eluting with a gradient of 0 to 40% NH$_3$/H$_2$O, to give neamine dimer 14 (3.4 mg, 26%). $^1$H NMR (500 MHz, D$_2$O) δ7.48–7.36 (10H, bs), 5.71 (2H, d, J=4 Hz), 4.34 (1H, d, J=16 Hz), 4.15 (1H, d, J=15 Hz), 3.95–3.32 (32H, m), 2.42–2.35 (2H, m), 1.76 (2H, dd, J=26, 13 Hz), 1.27–0.92 (20H, m); ES-MS (neg) calcd for C$_{60}$H$_{98}$N$_{12}$O$_{20}$ (M−H)$^-$ 1306, found 1306.

Epoxide 15. To 500 mg of perbenzyl-perazido-neamine (Greenberg, W. A.; et al. *J. Am. Chem. Soc.* 1999, 121, 6527)

(0.720 mmol) dissolved in 5 mL of THF was added 31.7 mg of 60% sodium hydride in paraffin (0.793 mmol). Freshly prepared (S)-glycidol triflate (121 mg, 0.793 mmol) was added and the solution stirred overnight at room temperature. The solution was quench with saturated NH$_4$Cl and partitioned with three 50 mL-aliquots of ethyl acetate. The solution was dried (MgSO$_4$) and concentrated under diminished pressure. The crude epoxide was purified by flash chromatography on silica gel (30×150 mm). The pure product was eluted with 6:1 hexanes-ethyl acetate to afford the epoxide 15 as a colorless foam: yield 405 mg (75%); TLC R$_f$ 0.32 (6:1 hexanes-ethyl acetate); mass spectrum (MALDIFTMS): m/z 775.3038 [M+Na$^+$] ($^C{}_{36}$H$_{40}$N$_{12}$O$_7$Na requires 775.3041).

Epoxide 16. To 280 mg of perbenzyl-perazido-neamine (Greenberg, W. A.; et al. *J. Am. Chem. Soc.* 1999, 121, 6527) (0.403 mmol) dissolved in 5 mL of THF was added 17.8 mg of 60% sodium hydride in paraffin (0.444 mmol). Freshly prepared (R)-glycidol triflate (65.3 mg, 0.444 mmol) was added and the solution stirred overnight at room temperature. The solution was quench with saturated NH$_4$Cl and partitioned with three 50 mL-aliquots of ethyl acetate. The solution was dried (MgSO$_4$) and concentrated under diminished pressure. The crude epoxide was purified by flash chromatography on silica gel (30×150 mm). The pure product was eluted with 6:1 hexanes-ethyl acetate to afford the epoxide 16 as a colorless foam: yield: 280 mg (92%); TLC R$_f$ 0.32 (6:1 hexanes-ethyl acetate); mass spectrum (ESI): m/z 775 [M+Na$^+$] (C$_{36}$H$_{40}$N$_{12}$O$_7$Na requires 775).

Protected Monomer 17. yield: 50.6 mg (65%), TLC R$_f$ 0.31 (2:2:96 triethylamine-methanol-dichloromethane); mass spectrum (MALDIFTMS): m/z 784.3616 [M+H$^+$] (C$_{37}$H$_{46}$N$_{13}$O$_7$ requires 784.3643).

Protected Monomer 18. yield: 52.0 mg (66.7%); TLC R$_f$ 0.31 (2:2:96 triethylamine-methanol-dichloromethane); (MALDIFTMS), m/z 784.3632 [M+H$^+$] (C$_{37}$H$_{46}$N$_{13}$O$_7$ requires 784.3643). Protected Dimer 19. yield: 33.2 mg (72%), TLC R$_f$ 0.38 (2:2:96 triethylamine-methanol-dichloromethane); mass spectrum (MALDIFTMS): m/z 1536.6846 [M+H$^+$] (C$_{73}$H$_{86}$N$_{25}$O$_{14}$ requires 1536.6786).

Protected Dimer 20. yield: 37.5 mg (73.4%); TLC R$_f$ 0.38 (2:2:96 triethylamine-methanol-dichloro-methane); (MALDIFTMS), m/z 1536.6711 [M+H$^+$] (C$_{73}$H$_{86}$N$_{25}$O$_{14}$ requires 1536.6785).

Protected Dimer 21. yield: 39.2 mg (74%), TLC R$_f$ 0.38 (2:2:96 triethylamine-methanol-dichloromethane); mass spectrum (MALDIFTMS): m/z 1593.7404 [M+H$^+$] (C$_{76}$H$_{13}$N$_{26}$O$_{14}$ requires 1593.7365).

Protected Dimer 22. yield: 29.3 mg (54.9%), TLC R$_f$ 0.38 (2:2:96 triethylamine-methanol-dichloromethane); (MALDIFTMS): m/z 1607.7503 [M+H$^+$] (C$_{77}$H$_{95}$N$_{26}$O$_{14}$ requires 1607.7521).

Protected Dimer 23. yield: 29.2 mg (54%), TLC R$_f$ 0.38 (2:2:96 triethylamine-methanol-dichloromethane); mass spectrum (MALDIFTMS): m/z 1621.7658 [M+H$^+$] (C$_{78}$H$_{76}$N$_{26}$O$_{14}$ requires 1621.7678).

Protected Dimer 24. yield: 31.2 mg (58%), TLC R$_f$ 0.38 (2:2:96 triethylamine-methanol-dichloromethane); (MALDIFTMS): m/z 1637.7633 [M+H$^+$] (C$_{78}$H$_{97}$N$_{26}$O$_{15}$ requires 1637.7627).

Protected Dimer 25. yield: 42.9 mg (90%); TLC R$_f$ 0.30 (2:2:96 triethylamine-methanol-dichloromethane); (MALDIFTMS), m/z 1593.7299 [M+H$^+$] (C$_{76}$H$_{93}$N$_{26}$O$_{14}$ requires 1593.7365).

Protected Dimer 26. yield: 37.5 mg (77.9%); TLC R$_f$ 0.26 (2:2:96 triethylamine-methanol-dichloromethane); (MALDIFTMS), m/z 1607.7531 [M+H$^+$] (C$_{77}$H$_{95}$N$_{26}$O$_{14}$ requires 1607.7521).

Protected Dimer 27. yield: 8.2 mg (17.0%), TLC R$_f$ 0.23 (2:2:96 triethylamine-methanol-dichloromethane); (MALDIFTMS), m/z 1621.7526 [M+H$^+$] (C$_{78}$H$_{97}$N$_{26}$O$_{14}$ requires 1621.7677).

Protected Dimer 28. yield: 8.2 mg (16.7%); TLC R$_f$ 0.29 (2:2:96 triethylamine-methanol-dichloromethane); mass spectrum (MALDIFTMS): m/z 1637.7633 [M+H$^+$] (C$_{78}$H$_{17}$N$_{26}$O$_{15}$ requires 1637.7627).

Monomer 17. yield: 4.5 mg (34%); TLC R$_f$ 0.29; (8:2:5:4 ammonium hydroxide-chloroform-ethanol-butanol); (MALDIFTMS), m/z 410.2596 [M+H$^+$] (C$_{16}$H$_{36}$N$_5$O$_7$ requires 410.2609).

Monomer 18. yield: 14.8 mg (47%); TLC R$_f$ 0.27; (8:2:5:4 ammonium hydroxide-chloroform-ethanol-butanol); (MALDIFTMS), m/z 432.2421 [M+Na$^+$] (C$_{16}$H$_{35}$N$_5$O$_7$Na requires 432.2429).

Dimer 19. yield: 6.3 mg (35%); TLC R$_f$ 0.21; (8:2:5:4 ammonium hydroxide-chloroform-ethanol-butanol); (MALDIFTMS), m/z 788.4761 [M+H$^+$] (C$_{31}$H$_{66}$N$_9$O$_{14}$Na requires 788.4729).

Dimer 20. yield: 4.9 mg (26%); TLC R$_f$ 0.24; (8:2:5:4 ammonium hydroxide-chloroform-ethanol-butanol); (MALDIFTMS), m/z 810.4514 [M+Na$^+$] (C$_{31}$H$_{65}$N$_9$O$_{14}$Na requires 810.4543).

Dimer 21. yield: 5.9 mg (57%); TLC R$_f$ 0.27; (8:2:5:4 ammonium hydroxide-chloroform-ethanol-butanol); (ESI), m/z 843 [M−H$^-$] (C$_{34}$H$_{75}$N$_{10}$O$_{14}$ requires 843).

Dimer 22. yield: 8.1 mg (99%); TLC R$_f$ 0.29; (8:2:5:4 ammonium hydroxide-chloroform-ethanol-butanol); (ESI), m/z 859 [M+H$^+$] (C$_{35}$H$_{75}$N$_{10}$O$_{14}$ requires 859).

Dimer 23. yield: 2.6 mg (16%); TLC R$_f$ 0.27; (8:2:5:4 ammonium hydroxide-chloroform-ethanol-butanol); (MALDIFTMS), m/z 895.5439 [M+Na$^+$] (C$_{36}$H$_{76}$N$_{10}$O$_{14}$ requires 895.5435).

Dimer 24. yield: 5.2 mg (41%); TLC R$_f$ 0.28; (8:2:5:4 ammonium hydroxide-chloroform-ethanol-butanol); (MALDIFTMS), m/z 889.5571 [M+H$^+$] (C$_{36}$H$_{77}$N$_{10}$O$_{15}$ requires 889.5564).

Dimer 25. yield: 6.0 mg (51%); TLC R$_f$ 0.26; (8:2:5:4 ammonium hydroxide-chloroform-ethanol-butanol); (ESI), m/z 843 [M−H$^-$] (C$_{34}$H$_{71}$N$_{10}$O$_{14}$ requires 843).

Dimer 26. yield: 3.1 mg (28%); TLC R$_f$ 0.29; (8:2:5:4 ammonium hydroxide-chloroform-ethanol-butanol); (ESI), m/z 859 [M+H$^+$] (C$_{35}$H$_{75}$N$_{10}$O$_{14}$ requires 859).

Dimer 27. yield: 13.0 mg (90%); TLC R$_f$ 0.27; (8:2:5:4 ammonium hydroxide-chloroform-ethanol-butanol); (MALDIFTMS), m/z 895.5439 [M+Na$^+$] (C$_{36}$H$_{76}$N$_{10}$O$_{14}$ requires 895.5435).

Dimer 28. yield: 8.1 mg (64%); TLC R$_f$ 0.27; (8:2:5:4 ammonium hydroxide-chloroform-ethanol-butanol); (MALDIFTMS), m/z 889.5565 [M+H$^+$] (C$_{36}$H$_{77}$N$_{10}$O$_{15}$ requires 889.5564).

What is claimed is:

1. A bifunctional antibiotic represented by the following structure:

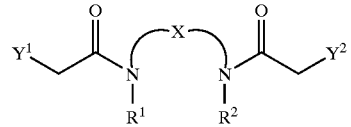

wherein:

Y$^1$ and Y$^2$ are a first and second pharmacophore respectively and are both represented by:

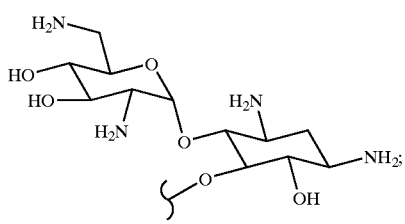

$R^1$ and $R^2$ are each independently selected from the group of radicals consisting of —H and —CH(Ph)CONHCH$_2$CO$_2$H; and X is the linkage and is selected from the group of diradicals consisting of —(CH$_2$)$_n$— and —[(CH$_2$)$_2$O(CH$_2$)$_3$]$_2$O, where $3 \leq n \leq 12$.

2. A bifunctional antibiotic represented by the following structure:

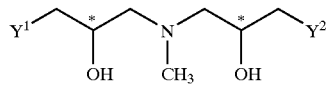

wherein $Y^1$ and $Y^2$ are a first and second pharmacophore respectively and are both represented by:

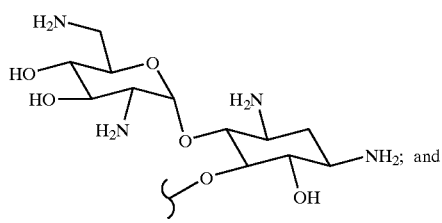

the stereochemistry is either (S,S) or (R,R).

3. A bifunctional antibiotic according to claim 2 represented by the following structure:

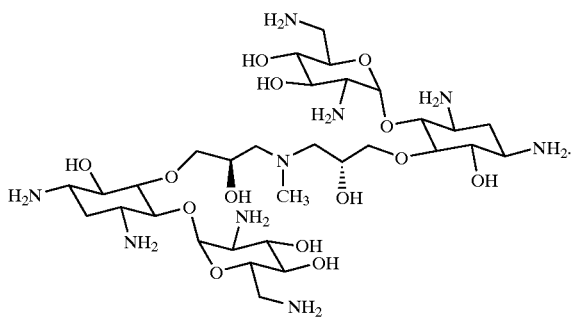

4. A bifunctional antibiotic according to claim 2 represented by the following structure:

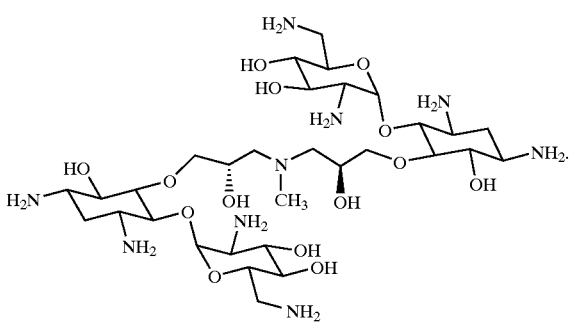

5. A bifunctional antibiotic represented by the following structure:

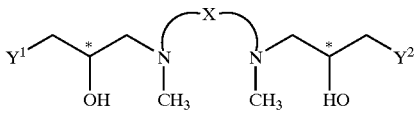

wherein:

$Y^1$ and $Y^2$ are a first and second pharmacophore respectively and are both represented by:

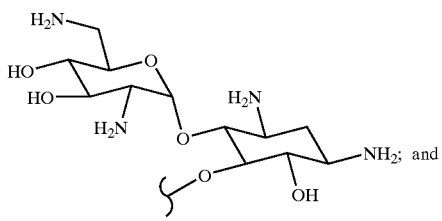

X is the linkage and is selected from the group of diradicals consisting of —(CH$_2$)$_n$— and —[(CH$_2$)$_2$]$_2$O, where $2 \leq n \leq 4$; and the stereochemistry is either (S,S) or (R,R).

6. A bifunctional antibiotic according to claim 5 represented by the following structure:

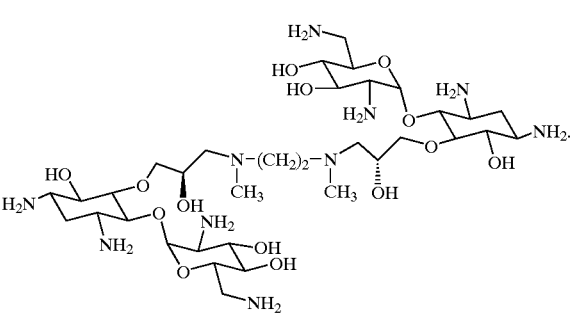

7. A bifunctional antibiotic according to claim 5 represented by the following structure:

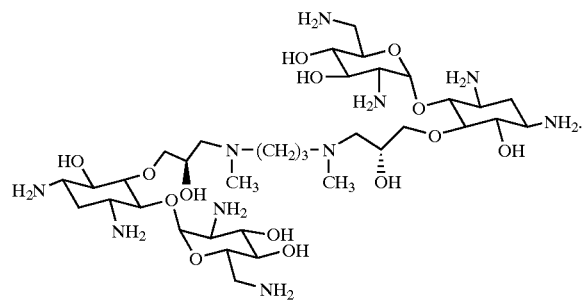

8. A bifunctional antibiotic according to claim 5 represented by the following structure:

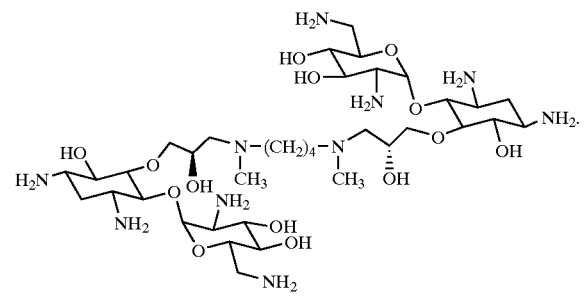

9. A bifunctional antibiotic according to claim 5 represented by the following structure:

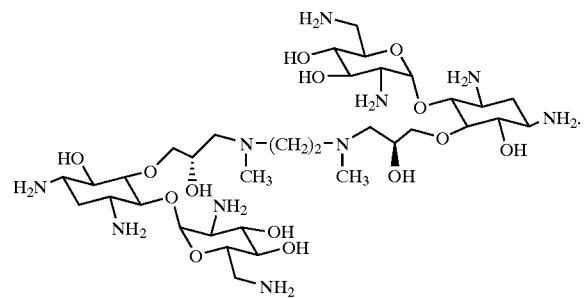

10. A bifunctional antibiotic according to claim 5 represented by the following structure:

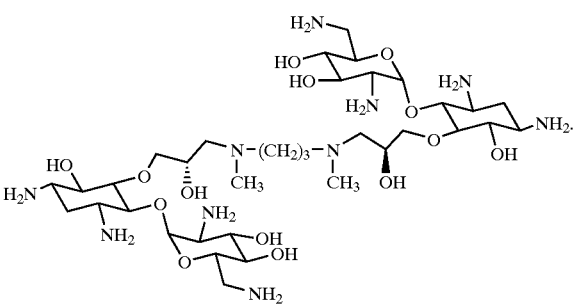

11. A bifunctional antibiotic according to claim 5 represented by the following structure:

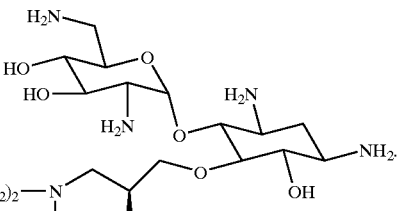

12. A bifunctional antibiotic according to claim 5 represented by the following structure:

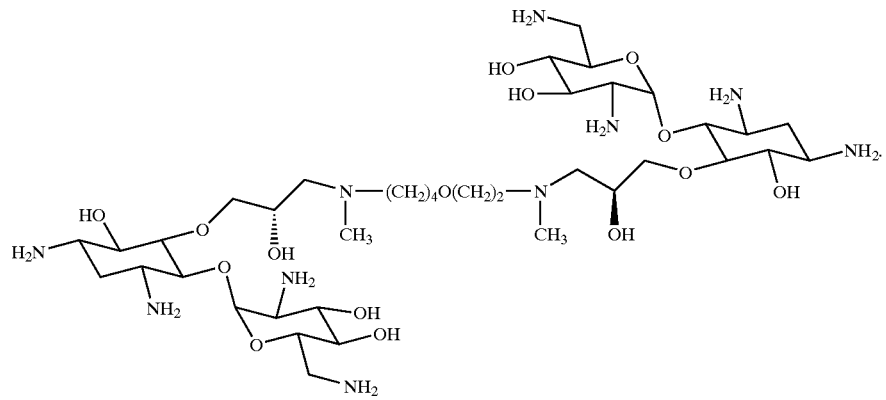

13. A bifunctional antibiotic according to claim 5 represented by the following structure:
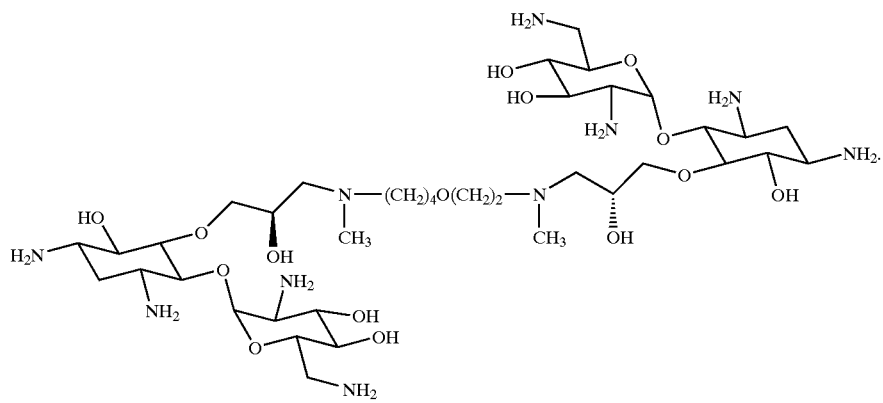
* * * * *

UNITED STATES PATENT AND TRADEMARK OFFICE
CERTIFICATE OF CORRECTION

PATENT NO. : 6,921,810 B2
DATED : July 26, 2005
INVENTOR(S) : Chi-Huey Wong and Steven Sucheck It is certified that error appears in the above-identified patent and that said Letters Patent is hereby corrected as shown below:

Column 1,
Line 5, insert -- This invention was made with Government support under Contract No. GM19404 by the National Institutes of Health. The Government has certain rights in the invention. --.

Signed and Sealed this

Twenty-fourth Day of January, 2006

JON W. DUDAS
*Director of the United States Patent and Trademark Office*